US012797125B2

(12) United States Patent
Sharma et al.

(10) Patent No.: US 12,797,125 B2
(45) Date of Patent: *Nov. 17, 2026

(54) SYSTEM AND METHOD FOR COMBINED ABLATION MODALITIES

(71) Applicant: Biosense Webster (Israel) Ltd., Yokneam (IL)

(72) Inventors: Tushar Sharma, Mission Viejo, CA (US); Assaf Govari, Haifa (IL); Andres Claudio Altmann, Haifa (IL); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 192 days.

This patent is subject to a terminal disclaimer.

(21) Appl. No.: 18/597,410

(22) Filed: Mar. 6, 2024

(65) Prior Publication Data

US 2024/0350192 A1 Oct. 24, 2024

Related U.S. Application Data

(60) Provisional application No. 63/496,218, filed on Apr. 14, 2023.

(51) Int. Cl.
*A61B 18/14* (2006.01)
*A61B 90/00* (2016.01)
(Continued)

(52) U.S. Cl.
CPC .......... *A61B 18/1492* (2013.01); *A61B 90/06* (2016.02); *A61B 2018/00357* (2013.01);
(Continued)

(58) Field of Classification Search
CPC ...... A61B 18/1492; A61B 2018/00351; A61B 2018/00357; A61B 2018/00375;
(Continued)

(56) References Cited

U.S. PATENT DOCUMENTS 5,391,199 A 2/1995 Ben-Haim
5,443,489 A 8/1995 Ben-Haim
(Continued)

FOREIGN PATENT DOCUMENTS

CN 114869455 A 8/2022
WO 2023009586 A1 2/2023

OTHER PUBLICATIONS

Extended European Search Report and Opinion dated Sep. 24, 2024, from corresponding European Application No. 24169840.6.
(Continued)

*Primary Examiner* — Michael F Peffley

(57) ABSTRACT

The disclosed technology includes a method of treating atrial fibrillation in a predetermined group of patients meeting predetermined inclusion and exclusion criteria, including delivering a catheter into a pulmonary vein of each patient of the predetermined group of patients, ablating one or more locations of targeted tissues of the pulmonary vein using the catheter, determining an ablation index as a function of the measured contact force and number of pulsed electric field applications for each location of the one or more locations from the pulsed electric field ablation, and achieving a predetermined effectiveness rate of pulmonary vein isolation in the group of patients within an effectiveness evaluation period. The catheter can include a tip electrode configured to emit either a pulsed electric field or a radiofrequency signal to cardiac tissue and measure a contact force experienced by the tip electrode against cardiac tissue during pulsed electric field ablation.

20 Claims, 15 Drawing Sheets

(51) Int. Cl.
*A61B 18/00* (2006.01)
*A61B 18/12* (2006.01)

(52) U.S. Cl.
CPC ............... *A61B 2018/00577* (2013.01); *A61B 2018/00613* (2013.01); *A61B 2018/00642* (2013.01); *A61B 2018/00708* (2013.01); *A61B 2018/00714* (2013.01); *A61B 2018/00791* (2013.01); *A61B 2018/1253* (2013.01); *A61B 2018/126* (2013.01); *A61B 2018/1266* (2013.01); *A61B 2090/065* (2016.02); *A61B 2218/002* (2013.01)

(58) Field of Classification Search
CPC ........... A61B 2018/00577; A61B 2018/00613; A61B 2018/00642; A61B 2018/00708; A61B 2018/00714; A61B 2018/00791; A61B 2018/00839; A61B 2018/00875; A61B 2018/1253; A61B 2018/126; A61B 2018/1266; A61B 2090/065; A61B 2218/002; A61B 90/06
See application file for complete search history.

(56) References Cited

U.S. PATENT DOCUMENTS

| | | | | |
|---|---|---|---|---|
| 5,558,091 | A | 9/1996 | Acker et al. | |
| 5,906,614 | A | 5/1999 | Stern et al. | |
| 6,172,499 | B1 | 1/2001 | Ashe | |
| 6,239,724 | B1 | 5/2001 | Doron et al. | |
| 6,332,089 | B1 | 12/2001 | Acker et al. | |
| 6,484,118 | B1 | 11/2002 | Govari | |
| 6,618,612 | B1 | 9/2003 | Acker et al. | |
| 6,690,963 | B2 | 2/2004 | Ben-Haim et al. | |
| 6,788,967 | B2 | 9/2004 | Ben-Haim et al. | |
| 6,892,091 | B1 | 5/2005 | Ben-Haim et al. | |
| 7,306,593 | B2 | 12/2007 | Keidar et al. | |
| 7,536,218 | B2 | 5/2009 | Govari et al. | |
| 7,756,576 | B2 | 7/2010 | Levin | |
| 7,848,787 | B2 | 12/2010 | Osadchy | |
| 7,869,865 | B2 | 1/2011 | Govari et al. | |
| 8,357,152 | B2 | 1/2013 | Govari et al. | |
| 8,456,182 | B2 | 6/2013 | Bar-Tal et al. | |
| 9,492,639 | B2 | 11/2016 | Clark et al. | |
| 10,517,670 | B2 | 12/2019 | Bar-Tal et al. | |
| 10,688,278 | B2 | 6/2020 | Beeckler et al. | |
| 10,869,713 | B2 | 12/2020 | Govari | |
| 11,096,741 | B2 | 8/2021 | Govari et al. | |
| 11,540,877 | B2 | 1/2023 | Altmann et al. | |
| 2008/0045946 | A1 | 2/2008 | Vaska | |
| 2010/0069921 | A1* | 3/2010 | Miller ................ | A61B 18/1233 600/301 |
| 2016/0095653 | A1 | 4/2016 | Lambert et al. | |
| 2017/0014181 | A1 | 1/2017 | Bar-Tal et al. | |
| 2018/0221078 | A1* | 8/2018 | Howard .................. | G06F 30/20 |
| 2019/0038349 | A1* | 2/2019 | Koblish ............... | A61B 5/6885 |
| 2021/0085387 | A1 | 3/2021 | Amit et al. | |
| 2021/0145534 | A1 | 5/2021 | Kulstad et al. | |
| 2021/0177503 | A1 | 6/2021 | Altmann et al. | |
| 2021/0186604 | A1 | 6/2021 | Altmann et al. | |
| 2022/0008126 | A1 | 1/2022 | Tsoref et al. | |
| 2022/0044787 | A1 | 2/2022 | Kaufman et al. | |
| 2022/0133172 | A1* | 5/2022 | Ransbury ........... | A61B 18/1492 600/473 |
| 2022/0401146 | A1 | 12/2022 | Asconeguy et al. | |
| 2024/0115314 | A1* | 4/2024 | Falahatpisheh ........ | A61B 90/06 |

OTHER PUBLICATIONS

Mansour et al.; "Persistent Atrial Fibrillation Ablation With Contact Force-Sensing Catheter", Jacc: Clinical Electrophysiology, vol. 6, No. 8, pp. 958-969, Dec 2020.
Chinese Search Report dated Aug. 25, 2023, from Chinese Application No. 202310948832.5.

* cited by examiner

| Investigational Device | Function |
|---|---|
| Catheter 14 | Transmits energy to the target tissue. |
| Generator 50 | Delivers PF and RF energy to compatible ablation catheter |
| **Non-investigational Equipment** | **Function** |
| CARTO™ 3 SYSTEM V7.9 workstation | For mapping and visualization information with software for PF and RF |
| nGEN™ Pump | Delivers heparinized saline to the catheter |
| Sterile Catheter Connection Cable (CR3434CT) | Connects the STSF Catheter with the TRUPULSE™ Generator. |
| SmartAblate Irrigation Tubing Sets (SAT001) | Delivers heparinized saline to the catheter |
| BW Multi-Electrode mapping Catheter | • Pre-ablation recording and mapping of the atria of the heart with the CARTO™ 3 System.<br>• Confirmation of entrance block |
| ≥8.5 Fr compatible sheath used with STSF catheter. | Facilitate deployment of catheter into the atria. |
| Adhesive electrical dispersive pads/indifferent split electrode (with a surface area of ≥ 124 $cm^2$ that conform with IEC/EN 60601-2-2) | Component of the RF / PF current return path (Valley Lab recommended) |
| EP Lab Recording Equipment | Records multiple intracardiac electrograms and signals from Generator 50 and performs electrical stimulation. |
| Esophageal Temperature Monitoring Device (OPTIONAL) | Esophageal temperature monitoring |

FIG. 5

| | |
|---|---|
| Mild | Awareness of signs, symptoms, or events that are otherwise easily tolerated that may result in minimal transient impairment of a body function or damage to a body structure, but do not require intervention other than monitoring |
| Moderate | Any event that results in moderate transient impairment of a body function or damage to a body structure that causes interference with usual activities, or that warrants possible intervention, such as the administration of medication, to prevent permanent impairment of a body function or damage to a body structure |
| Severe | Any event that is incapacitating (an inability to do usual activities) or is life-threatening and results in permanent impairment of a body function or damage to a body structure, or requires intervention, such as major surgery, to prevent permanent impairment of a body function or damage to a body structure |

FIG. 7

| | PF Mode | RF Mode |
|---|---|---|
| Idle Mode | 2 ml/min | 2 ml/min |
| During Ablation | 4 ml/min | Dependent on target power:<br>≤30W: 8ml/min<br>>30W: 15ml/min |

FIG. 8

| Assessments | Pre-Procedure | Pre-Discharge | Follow-up | | | | | |
|---|---|---|---|---|---|---|---|---|
| | | | 7 Day | 1 Month | 3 Month | 6 Month | 12 Month | UNS |
| Study Day | | | D7 | D30 | D90 | D180 | D365 | |
| Visit window | | | D7-D9 | D23-D37 | D76-D104 | D166-D194 | D335-D379 | |
| Clinic visit | • | • | • | • | • | • | • | • |
| Phone call | | | • | | | | | |
| Patient Informed Consent | • | | | | | | | |
| Demographics | • | | | | | | | |
| Medical History | • | | | | | | | |
| Pregnancy test | • | | | | | | | |
| LA and LVEF assessment | • | | | | | | | |
| Left atrial thrombus detection | • | | | | | | | |
| Pericardial fluid assessment | | • | | | | | | |
| 12 Lead ECG | • | • | | • | • | • | • | • |
| Atrial Arrhythmia monitoring (Remote) | | | | • | • | • | • | • |
| Atrial Arrhythmia monitoring (24-hr Holter) | | | | | • | • | • | • |
| Repeat ablations | | | • | • | • | • | • | • |
| Concomitant Medication | • | • | • | • | • | • | • | • |
| Device Deficiencies | | • | | | | | | |
| Adverse Events | • | • | • | • | • | • | • | • |
| AFEQT | • | | | | • | • | • | |
| Cardiac CT/MRA | • | | | | • | | | |

FIG. 9

| Assessments | Pre-Procedure | Pre-Discharge | Follow-up | | | | | |
|---|---|---|---|---|---|---|---|---|
| | | | 7 Day | 1 Month | 3 Month | 6 Month | 12 Month | UNS |
| PV Durability Subset | | | | | | | | |
| 3D Electro anatomical mapping | • | | | | • | | | |
| Endoscopy Subset | | | | | | | | |
| Endoscopy | | • | | | | | | |
| Neurological Subset | | | | | | | | |
| Cerebral MRI | • | • | | • | • | • | • | • |
| Neurological Exam | • | • | | • | • | • | • | • |
| NIH Stroke Scale | • | • | | • | • | • | • | • |
| mRS | • | | | • | • | • | • | • |
| MMSE | • | | | • | • | • | • | • |

FIG. 10

SYSTEM AND METHOD FOR COMBINED ABLATION MODALITIES

CROSS REFERENCE TO RELATED APPLICATIONS

This application claims the benefit of priority under 35 U.S.C. § 119 to prior filed U.S. Provisional Patent Application No. 63/496,218, filed Apr. 14, 2023, the entire contents of which is hereby incorporated by reference as if set forth in full herein.

FIELD

This disclosure relates to devices and methods of performing pulsed field ablation within or near a heart. The devices and methods may also be useful for mapping and/or thermal ablation using radio frequency electrical signals.

BACKGROUND

Cardiac arrhythmias, such as atrial fibrillation (AF), occur when regions of cardiac tissue abnormally conduct electric signals to adjacent tissue, thereby disrupting the normal cardiac cycle and causing asynchronous rhythm. Sources of undesired signals are typically located in tissue of the atria and ventricles. Regardless of source, unwanted signals are conducted elsewhere through heart tissue where they can initiate or continue arrhythmia.

Treatment of cardiac arrhythmia can include disrupting the conducting pathway of electrical signals causing arrhythmia to cease or modify the propagation of unwanted electrical signals from one portion of the heart to another. Such procedures typically include a two-step process: (1) mapping; and (2) ablation. During mapping, a catheter having an end effector having preferably a high density of electrodes is moved across target tissue, electrical signals are acquired from each electrode, and a map is generated based on the acquired signals. During ablation, non-conducting lesions are formed at regions selected based on the map to disrupt electrical signals through those regions. Presently the most common ablation technique involves applying radio frequency (RF) electrical signals via electrodes to tissue to generate heat. Irreversible electroporation (IRE) ablation is a more recently developed technique which involves applying short duration high voltage pulses across tissue to cause cell death, sometimes referred to as pulsed field ablation (PFA). Typically, RF and PFA are applied as separate and distinct techniques. The lesion created by PFA ablation is related to the parameters of the pulses, the number of PFA applications as well as the contact force at which the ablation electrodes are pressed against the tissue wall. Typically, the parameter of the pulses is preset, e.g., amplitude, duration, number of pulses in a train, etc. and the number of PFA applications as well as the contact force can be manipulated by the user; however, a user may not be sure how much contact force and/or number of applications is needed to obtain a desired lesion depth.

Previous solutions have used two or more separate catheters (e.g., one for the electropotentials and temperature measurements, and another for the ablation) with no indication of desired lesion depth. Embodiments disclosed herein facilitate the two measurements, enable ablation using radiofrequency electromagnetic energy using a single catheter, and in addition predict a PFA ablation index before ablation is initiated.

SUMMARY

Generally, examples presented herein can include a method for treating atrial fibrillation. The method can include treating atrial fibrillation in a predetermined group of patients meeting predetermined inclusion and exclusion criteria, including delivering a catheter into a pulmonary vein of each patient of the predetermined group of patients, ablating one or more locations of targeted tissues of the pulmonary vein using the catheter, determining an ablation index as a function of the measured contact force and number of pulsed electric field applications for each location of the one or more locations from the pulsed electric field ablation, and achieving a predetermined effectiveness rate of pulmonary vein isolation in the group of patients within an effectiveness evaluation period. The catheter can include a tip electrode configured to emit either a pulsed electric field or a radiofrequency signal to cardiac tissue and measure a contact force experienced by the tip electrode against cardiac tissue during pulsed electric field ablation.

An exemplary embodiment of the present disclosure includes a system for applying pulsed field ablation to treat atrial fibrillation in a group of patients. The system can include a catheter and a processor. The catheter can include a tip electrode configured to emit a pulsed electric field or a radiofrequency signal to cardiac tissue and ablate one or more locations of cardiac tissue of the pulmonary vein. The processor can be configured to measure a contact force experienced by the tip electrode against cardiac tissue during pulsed electric field ablation, and determine a pulsed field ablation index as a function of the measured contact force and number of pulsed electric field applications for each location of the one or more locations. The system can be configured to achieve a predetermined effectiveness rate of pulmonary vein isolation in the group of patients within an effectiveness evaluation period.

An exemplary embodiment of the present disclosure includes a focal ablation catheter. The focal ablation catheter can include a tubular member extending along a longitudinal axis between a handle, a contact force sensor, and a tip electrode at a distal end of the tubular member. The tip electrode can be electrically connected to an energy generator configured to emit either a pulsed electric field or a radiofrequency signal to cardiac tissue through the tip electrode at one or more locations of cardiac tissue under control of a processor to ablate cardiac tissue. The contact force sensor can be physically connected to the tip electrode and electrically connected to the processor to provide indication of a contact force experienced by the tip electrode against cardiac tissue during pulsed electric field ablation so that an ablation index is determined as a function of the measured contact force of the tip electrode and number of pulsed electric field applications for each location of the one or more locations in a heart.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 5 is a table summarizing required study devices and function, in accordance with the disclosed technology.

FIG. 7 shows a table summarizing intensity or severity of each AE assessed according to classifications, in accordance with the disclosed technology.

FIG. 8 is a table summarizing recommended operating flow settings for a catheter, in accordance with the disclosed technology.

FIG. 9 is a table summarizing subject treatment and follow-up schedule for the study, in accordance with the disclosed technology.

FIG. 10 is a table summarizing subject treatment and follow-up schedule for PV durability, endoscopy, and neurological subsets for the study, in accordance with the disclosed technology.

DETAILED DESCRIPTION

Figure 1:
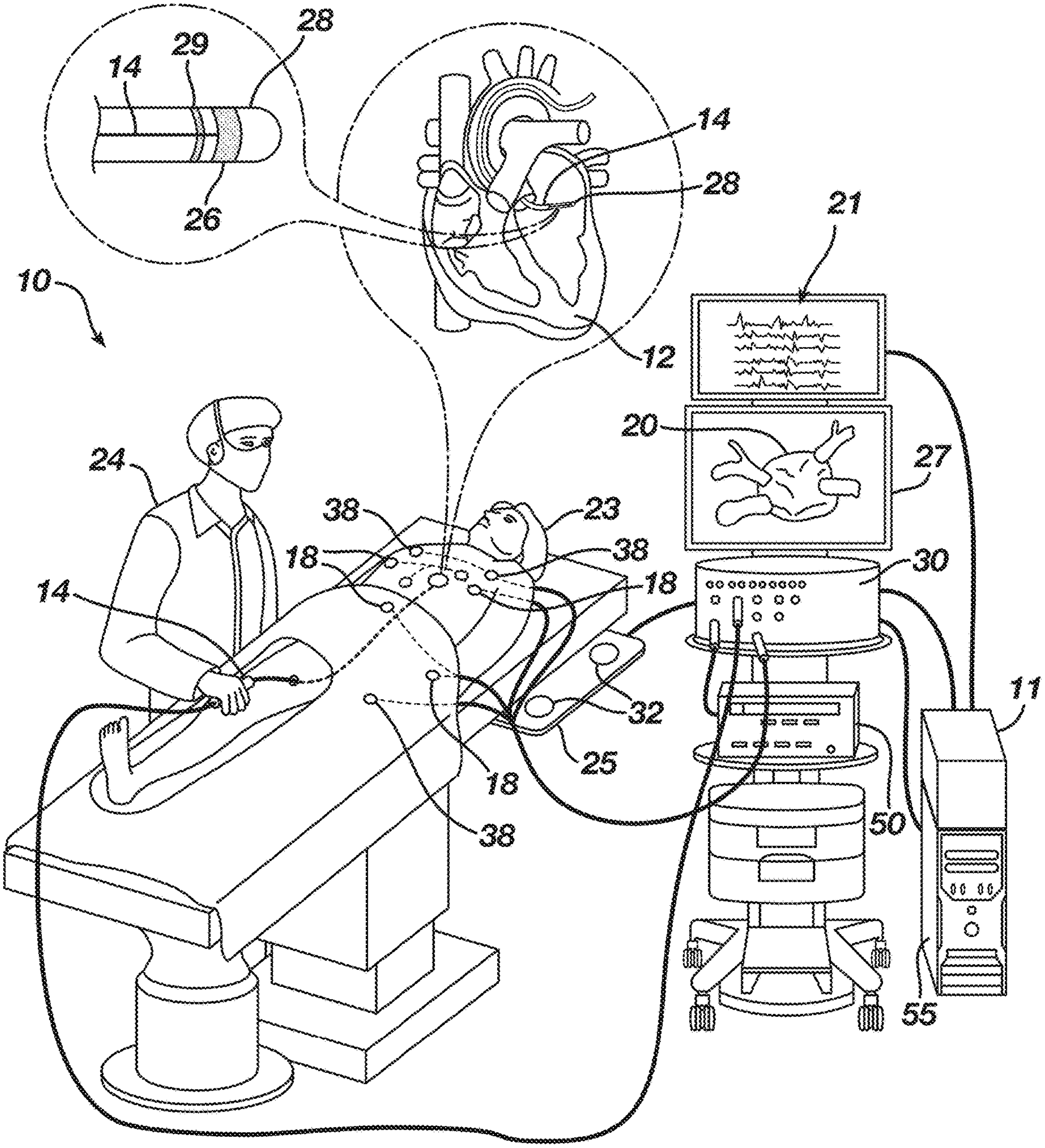
FIG. 1 is a schematic pictorial illustration of a medical system including an example medical probe which can be used in accordance with the disclosed technology.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways. Features of embodiments disclosed herein, including those disclosed in the Appendix included with priority application U.S. Patent Application No. 63/496,218, can be combined as understood by a person skilled in the pertinent art according to the teachings herein.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values ±20% of the recited value, e.g. "about 90%" can refer to the range of values from 71% to 99%.

As discussed herein, vasculature of a "subject" or "patient" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, physician, surgeon, or any other individual or delivery instrumentation associated with delivery of a multi-electrode RF balloon catheter for the treatment of drug refractory atrial fibrillation to a subject.

As discussed herein, "NIHSS Score" means The National Institutes of Health Stroke Scale, or NIH Stroke Scale (NIHSS) and is a tool used by healthcare providers to objectively quantify the impairment caused by a stroke. The NIHSS is composed of 11 items, each of which scores a specific ability between a 0 and 4. For each item, a score of 0 typically indicates normal function in that specific ability, while a higher score is indicative of some level of impairment. The individual scores from each item are summed in order to calculate a patient's total NIHSS score. The maximum possible score is 42, with the minimum score being a 0.

As discussed herein, "mRS" means the modified Rankin Scale (mRS) that is a commonly used scale for measuring the degree of disability or dependence in the daily activities of people who have suffered a stroke or other causes of neurological disability. The mRS scale runs from 0-6, running from perfect health without symptoms to death. An mRS score of 0 is understood as no symptoms being observed. An mRS score of 1 is understood as no significant disability is observed and the patient is able to carry out all usual activities, despite some symptoms. An mRS score of 2 is understood as slight disability and the patient is able to look after own affairs without assistance, but unable to carry out all previous activities. An mRS score of 3 is understood as moderate disability whereby the patient can require some help but is able to walk unassisted. An mRS score of 4 is understood as moderate severe disability and the patient is unable to attend to own bodily needs without assistance or walk unassisted. An mRS score of 5 is understood as severe disability and the patient requires constant nursing care and attention, bedridden, incontinent. An mRS score of 6 is understood as the patient being deceased.

As discussed herein, the term "safety," as it relates to devices used in ablating cardiac tissue, related delivery systems, or method of treatment refers to a relatively low severity of adverse events, including adverse bleeding events, infusion or hypersensitivity reactions. Adverse bleeding events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration, EMEA or a corresponding national regulatory agency. For example, a clinical study can be an adequately sized, randomized, double-blinded controlled study used to clinically prove the effects of the cardiac ablation device(s) and related system(s) of this disclosure. Most preferably to clinically prove the effects of the device(s) with respect to all targeted pulmonary veins, for example, to achieve a clinically effective outcome in for the patient and/or achieve pulmonary vein isolation in those afflicted veins.

As discussed herein, the term "ablate" or "ablation," as it relates to the devices and corresponding systems of this disclosure, refers to components and structural features configured to reduce or prevent the generation of erratic cardiac signals. Non-thermal ablation includes use of irreversible electroporation (IRE) to cause cell death, referred throughout this disclosure interchangeably as pulsed electric field (PEF) and pulsed field ablation (PFA). Thermal ablation includes use of extreme temperature to cause cell death and includes RF ablation. Ablating or ablation as it relates to the devices and corresponding systems of this disclosure is used throughout this disclosure in reference to ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" as it generally relates to known methods, devices, and systems includes various forms of bodily tissue ablation as understood by a person skilled in the pertinent art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal having a positive-voltage phase pulse (referred to herein as "positive phase") and a negative-voltage phase pulse (referred to herein as "negative phase"). "Monophasic pulse" refers to an electrical signal having only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape having an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

Previous solutions have used two or more separate instructions (e.g., one for the electropotentials and temperature measurements, and another for the ablation), embodiments disclosed herein facilitate the two measurements, and in addition enable ablation using radiofrequency electromagnetic energy, using a single catheter. The catheter has a lumen, and a balloon is deployed through the catheter lumen (the balloon travels through the lumen in a collapsed, uninflated configuration, and the balloon is inflated on exiting the lumen). The balloon has an exterior wall or membrane and has a distal end and a proximal end which define a longitudinal axis that extends the lumen.

Reference is made to FIG. 1 showing an example catheter-based electrophysiology mapping and ablation system 10. To perform the ablation, the operator 24 inserts a delivery sheath catheter 14 through the patient's vascular system into a chamber or vascular structure of a heart 12. Typically, a delivery sheath catheter 14 is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating, and/or catheters dedicated for sensing, IRE, and ablating. Operator 24 can position a distal tip 28 of catheter 14 in contact with the heart wall for sensing a target site in heart 12. For ablation/IRE, operator 24 would similarly bring a distal end of a catheter to a target site. Ablation/IRE catheter 14 can be a multi-electrode radiofrequency balloon catheter for cardiac electrophysiological ablation of pulmonary veins of the atria and, when used with a multi-channel generator, for the treatment of drug refractory recurrent symptomatic PAF, as discussed more particularly below. Note that such catheters 24 can be introduced through the femoral artery, wrist artery (radial access) or directly through the carotid artery. While both radial and carotid access avoids the aortic arches, there are other drawbacks. However, all three approaches are considered to be known to ones of skill in this art.

Catheter 14 is an exemplary catheter that includes one and preferably multiple electrodes 26 optionally distributed over a plurality of spines (as shown in FIGS. 5A and 5C) at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of external magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof. Generator 50 is controlled via a processor disposed in workstation 55 to emit RF energy (e.g., sine waves) at a preset power level (in Watts) over a predetermined duration (less than 60 seconds). Likewise, generator 50 can be controlled by the processor in workstation 55 to emit pulsed field energy (e.g., square waves) at ultra short duration in various pulses.

Generator 50 can include a specialized device for delivering Radiofrequency (RF) or Pulsed Field (PF) energy through catheter 14. RF energy is delivered in power-controlled ablation mode at the selected power setting to a site in the heart via the study catheter. PF energy consists of a series of short duration, high voltage, high-frequency, unipolar, biphasic pulses (or “trains” of pulses) being applied to a site in the heart via the study catheter 14. The generator 50 delivers PF energy in predefined voltage, pulse length, and number of pulses, which have been optimized in pre-clinical testing to target cardiac tissue and produce durable lesions. The generator 50 is compatible with the Biosense Webster CARTO™ 3 System, nGEN™ Pump and standard electrophysiology (EP) lab equipment. Generator 50 is indicated for use in conjunction with compatible cardiac ablation catheters to deliver RF or PF energy during cardiac ablation procedures.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (5) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

Figure 2A:
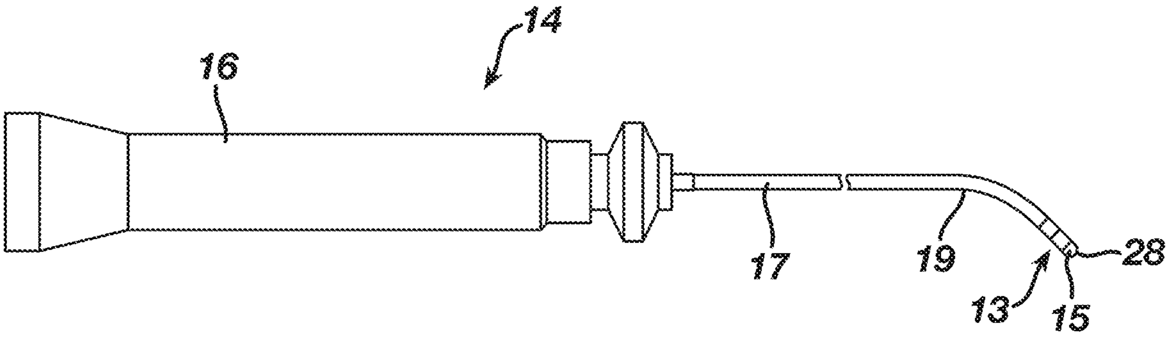
FIG. 2A is a side view of a catheter for use with the system of FIG. 1, in accordance with the disclosed technology.

As shown in FIG. 2A, the catheter 14 can include an elongated catheter body 17, a deflectable intermediate section 19, a distal section 13 carrying at least a tip electrode 15 on its distal tip end 28, and a control handle 16. The catheter 14 can be one that is a steerable multi-electrode luminal catheter with a deflectable tip designed to facilitate electrophysiological mapping of the heart 12 and to transmit radiofrequency (RF) and pulse field (PF) current to the tip electrode 15 for ablation purposes. An operator 24, such as a cardiologist, can insert catheter 14 through the vascular system of a patient 23 so that a distal section 13 of the catheter enters a chamber of the patient’s heart 12. The operator 24 advances the catheter so that a distal tip 28 of the catheter engages endocardial tissue at a desired location or locations. Catheter 14 is connected by a suitable connector at its proximal end to console 55. The console 55 may include the ablation energy generator 50, which supplies high-frequency electrical energy via the catheter 14 for ablating tissue in the heart 12 at the locations engaged by the distal section 13. For ablation, the catheter 14 can be used in conjunction with a dispersive pad (e.g., indifferent electrode). In this respect, the catheter 14 can include a shaft that measures 7.5 F with 8 F ring electrodes. The catheter 14 can also have a force-sensing system that provides a real-time measurement of contact force between the catheter tip and the heart 12 wall.

Figure 2B:
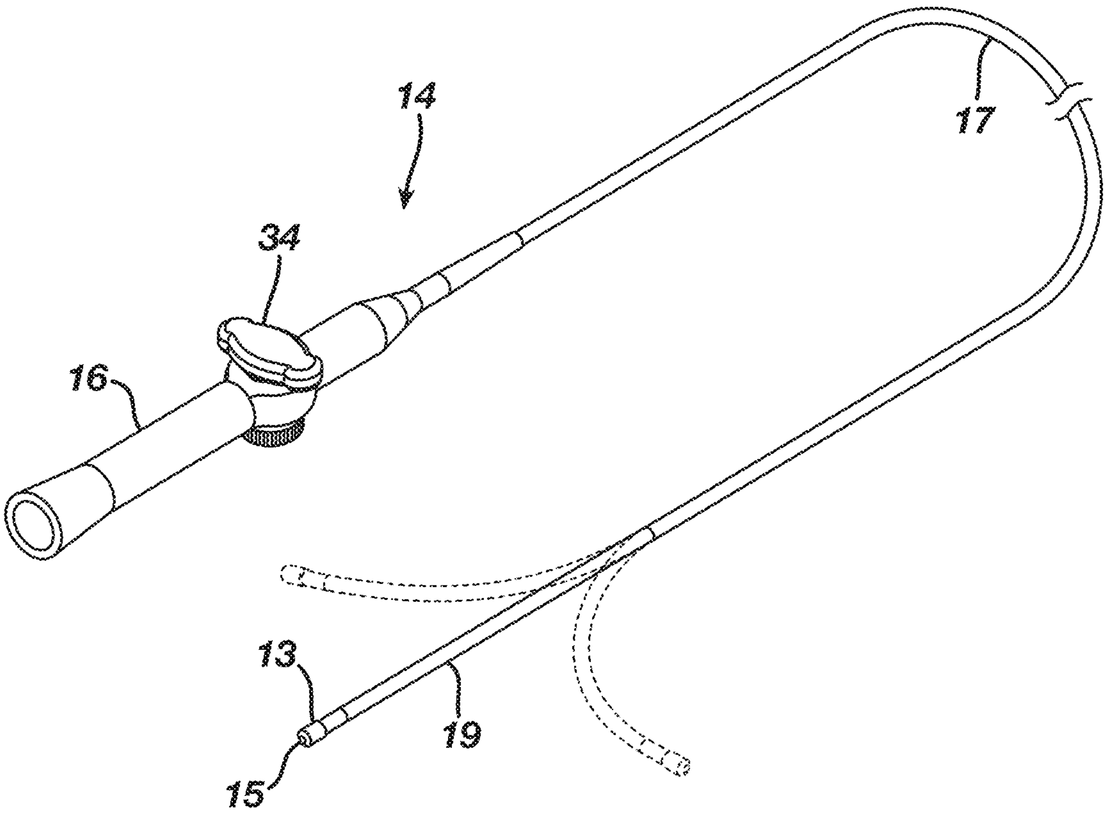
FIG. 2B is a perspective view of a catheter for use with the system of FIG. 1, in accordance with the disclosed technology.

As shown in FIG. 2B, distal tip section 13 can include an electrode assembly and at least one micro-element having an atraumatic distal end adapted for direct contact with target tissue. Catheter body 17 can have a longitudinal axis, and an intermediate section 19 distal of the catheter body 17 that can be uni- or bi-directionally deflectable off-axis from the catheter body 12. Distal of the intermediate section 19 is the electrode assembly carrying at least one micro-element. Proximal of the catheter body is control handle 16 that allows an operator to maneuver the catheter, including deflection of the intermediate section 14.

The elongated catheter body can be a relatively high torqueable shaft with the distal tip section 13 attached to the deflectable intermediate section 19 and containing an electrode assembly 15 with an array of electrodes. For example, the distal tip section 13 can include a 3.5 mm tip dome with three microelectrodes. All of the electrodes may be used for recording and stimulation purposes. A rocker lever 34 can be used to deflect the distal tip section 13. The high-torque shaft also allows the plane of the curved tip to be rotated to facilitate accurate positioning of the catheter tip at the desired site. Three curve type configurations designated "D," "F," and "J" are available. The electrode assembly 15 serves to deliver ablative energy from the ablation generator 50 to the desired ablation site. The electrode assembly 15 and ring electrodes can be made from noble metals. In some examples, the catheter 14 can also include six thermocouple temperature sensors that are embedded in the 3.5 mm tip electrode.

Figure 3A:
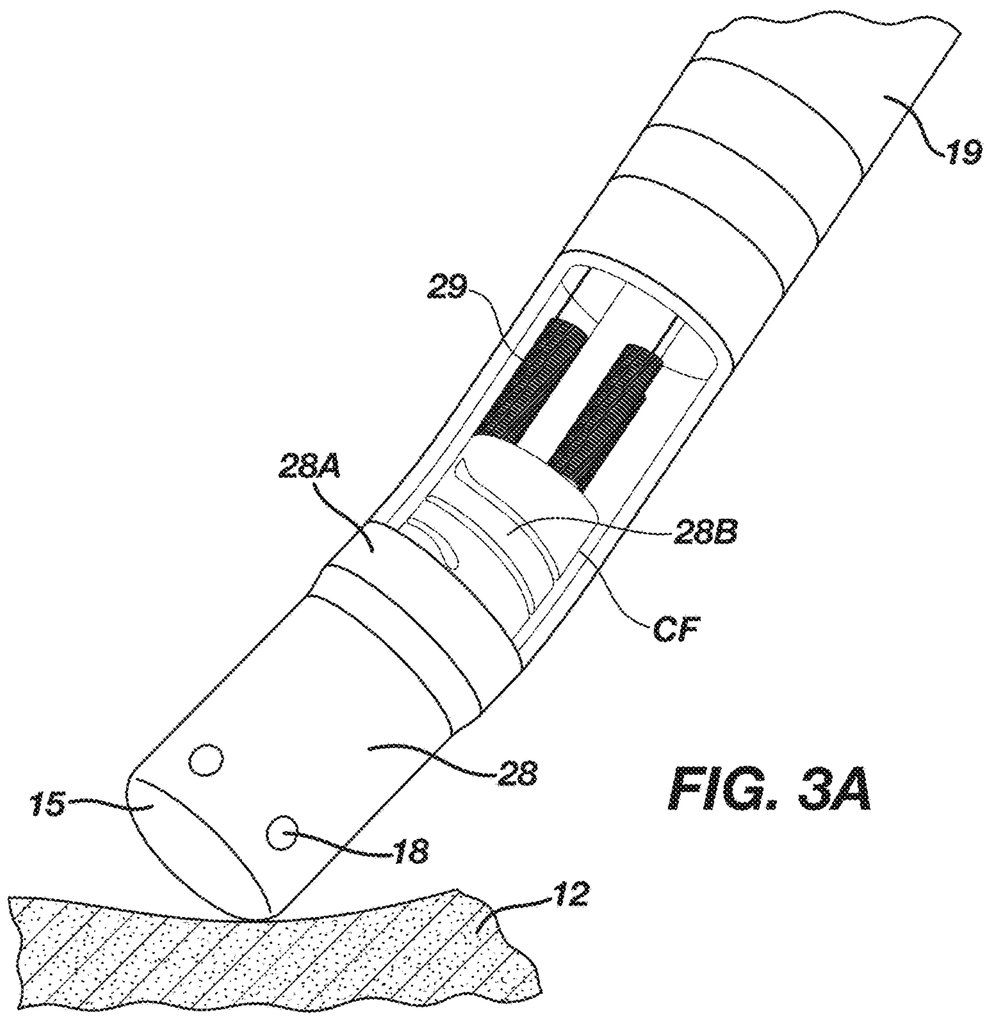
FIG. 3A is a perspective close up view of the catheter distal end with a tip electrode coupled to a contact force sensor, tri-axes location sensor and a catheter shaft.

FIG. 3A illustrates an exemplary end effector of the catheter 14 with a catheter shaft 19 coupled to a magnetic location sensor 29, contact force sensor CF and tip electrode 15. Tip electrode 15 is coupled to the CF sensor via a flexible coupling 28A for tip 28 so that force on tip electrode 15 is transmitted through tip 28 to the flexible coupling 28A which compresses spring 28B of the CF sensor. That is, when a force is applied to the contact force sensor CF via tip electrode 15, a magnetic field sensor disposed inside the CF can detect a change in the magnitude of the force of the magnetic field generated by a separate magnetic field generator coil disposed in the CF sensor. Because the spring constant K of the spring 28B can be predetermined and the distance between the magnetic field generator and the magnetic field sensor can be detected, the force applied to the tip electrode 15 can be determined (e.g., by using Hooke's law, or the equation F=d*K). Details relating to the CF sensor are shown and described in U.S. Pat. Nos. 8,357,152 and 10,688,278, which are incorporated by reference herein, as well as a copy included in the Appendix included with priority application U.S. Patent Application No. 63/496,218.

Figure 3B:
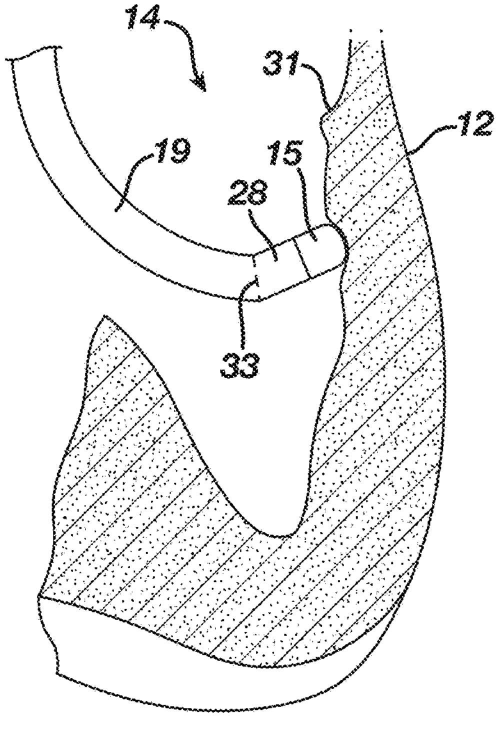
FIG. 3B is a schematic sectional view of a heart chamber with a catheter of FIG. 3A in contact with the heart wall inside the chamber, in accordance with the disclosed technology.

FIG. 3B is a schematic sectional view of a chamber of a heart 12, showing a flexible deflectable intermediate section 19 of a catheter 14 inside the heart 12. The catheter 14 is typically inserted into the heart percutaneously through a blood vessel, such as the vena cava or the aorta. The electrode 15 on a distal tip 28 of the catheter engages endocardial tissue 31. Pressure exerted by the distal tip against the endocardium deforms the endocardial tissue locally, so that electrode 15 contacts the tissue over a relatively large area. In the pictured example, the electrode 15 engages the endocardium at an angle, rather than head-on. Distal tip 28 therefore bends at an elastic joint 33 relative to deflectable intermediate section 19 of the catheter. The bend facilitates optimal contact between the electrode and the endocardial tissue.

Because of the elastic quality of joint 33, the angle of bending of the joint is typically proportional to the pressure exerted by tissue 30 on distal tip 28 (or equivalently, the pressure exerted by the distal tip on the tissue). Measurement of the bend angle thus gives an indication of this pressure. The pressure indication via contact force sensor CF may be used by the operator of catheter 14 to ensure that the distal tip is pressing against the endocardium firmly enough to give the desired therapeutic or diagnostic result, but not so hard as to cause undesired tissue damage. U.S. Pat. Nos. 8,357,152, 9,492,639 and 10,688,278 whose disclosures are incorporated herein by reference with a copy in the Appendix included with priority application U.S. Patent Application No. 63/496,218, describes a system that uses a pressure-sensing catheter in this manner. Catheter 14 may be used in such a system.

Ablation energy generator 50 can generate radio frequency (RF) current pursuant to known RF generators as disclosed in U.S. Pat. Nos. 5,906,614 and 10,869,713 which discloses high power RF generators, both disclosures are incorporated herein by reference with a copy provided in the Appendix included with priority application U.S. Patent Application No. 63/496,218. RF current creates ablation lesions by a thermal process. RF ablation raises tissue temperature and destroys cells through heating. Further, ablation energy generator 50 can also generate pulse field (PF) current to create lesions using irreversible electroporation (IRE). IRE is a predominantly non-thermal process that destroys cells by disrupting the cell membranes. Discussions of a dual mode ablation energy generator 50 capable of producing both RF and PF signals can be found in U.S. Pat. No. 11,540,877, further discussing using PF and RF ablation in combination and is incorporated herein by reference with a copy provided in the Appendix included with priority application U.S. Patent Application No. 63/496,218.

System Components, Setup, and Connectivity

To conduct an electrophysiology procedure of the present disclosure, the Catheter 14 can include THERMOCOOL SMARTTOUCH™ SF Bi-Directional Navigation Catheter (available from Biosense Webster, Inc. of Irvine, California) and Generator 50 can include TRUPULSE™ Generator (available from Biosense Webster, Inc. of Irvine, California) in combination with one or more of the following CE marked devices, available from Biosense Webster, Inc. of Irvine, California:

- nGEN™ Pump (D139701)
- SmartAblate Irrigation Tubing Sets (SAT001)
- Patient Interface Unit (PIU) of CARTO™ 3 system
- CARTO™ 3 System and CARTO™ V7.9 workstation
- Sterile Catheter Connection Cable (CR3434CT)
- Multi-electrode mapping Catheter
- ≥8.5Fr Compatible Sheath The following devices, CE marked by other companies, are also required for the procedure:

- ≥8.5Fr Compatible Sheath
- Electrophysiology (EP) Recording System
- Stimulator
- Body Surface Electrocardiogram (ECG) Patches and Leads
- Indifferent electrode patches
- Fluoroscopy/X-Ray System
- Cardiac Defibrillator
- Intracardiac Ultrasound (Investigator preference, not required)

Figure 4A:
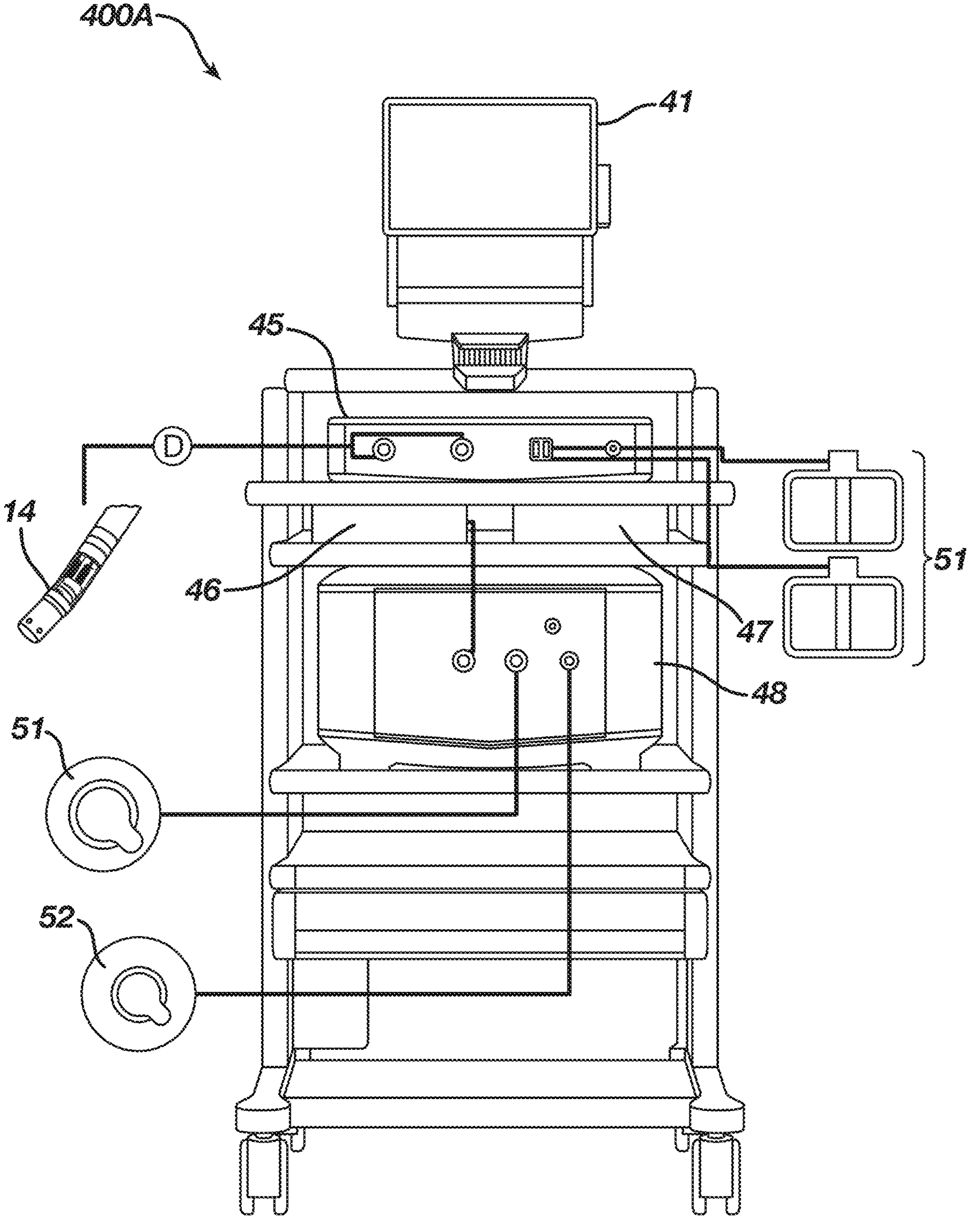
FIGS. 4A and 4B are connectivity diagrams for system set-up, including front view (FIG. 4A) and back view (FIG. 4B), in accordance with the disclosed technology.
Figure 4B:
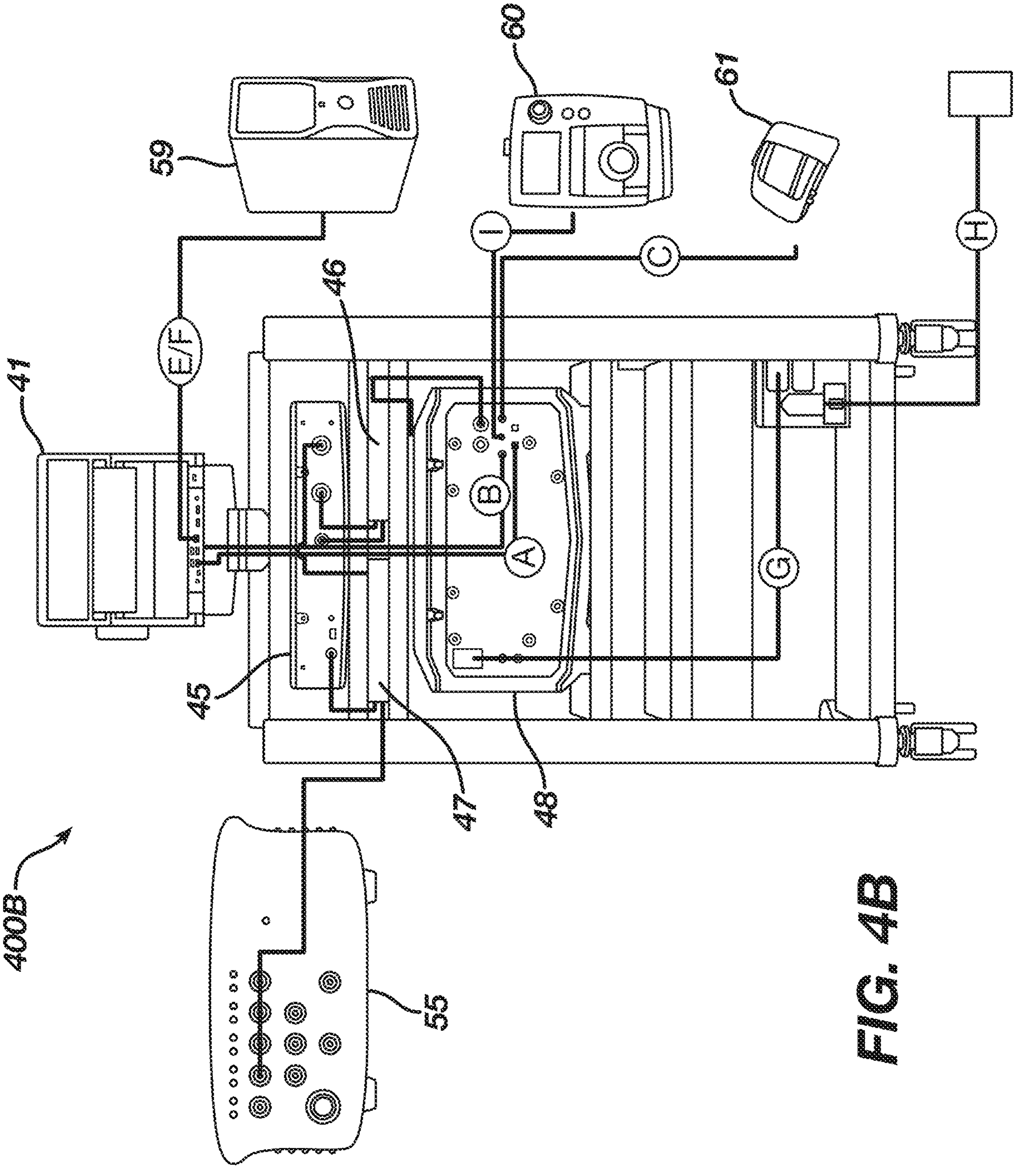

For the study, each site will have a clinical investigation plan that specifies devices required for study participation. In addition, device set-up must be completed per the instructions for use and user manual. FIGS. 4A and 4B illustrate a connectivity diagram from the front view (FIG. 4A) and the back view (FIG. 4B) for system set up and connectivity of system 400. As shown in the front view, system 400A includes a monitor 41, catheter 14, a console intercommunications unit (CIU) 45, an interface box 46, CARTO™ Relay Box 47, a console 48, indifferent electrodes 49, a safety plug for CARTO™ connector 51, and a safety plug for ECG connector 52. In the back view, system 400B includes monitor 41, CIU 45, interface box 46, CARTO™ Relay Box 47, console 48, indifferent electrodes 49, a CARTO™ System PIU 54, CARTO™ 3 workstation 55, nGEN™ pump 60, and a pedal 61. The CARTO™ System PIU is where the cable connections to the patient are made. Generator 50 system comprises a console, monitor, pedal, connection interface unit (CIU) and cables. The console contains the hardware that controls the delivery of energy. The monitor contains a touch screen user interface. It also contains the software that communicates with the generator and external devices. The monitor allows the user to set parameters for the generator and control when energy is delivered. The monitor is connected directly to the console. The pedal is an alternate way to start and stop ablation. The CIU connects the catheter and indifferent electrodes and enables the interface to the CARTO™ system. There is also a cable connecting the generator components to each other and to other devices. A summary of the required devices and function are provided in FIG. 5.

Typical RF ablation creates lesions with a depth/size of about 3 mm to about 5 mm. One example of the parameters used to create the RF ablated lesions are setting a power of the RF signal to about 1 Watt to about 400 Watts. Further, the RF signal is maintained for about 1 second to about 60 seconds. Given that RF ablation uses heat to damage the tissue, RF signals typically generate a temperature change in the tissue from about 20° C. to about 70° C. This temperature change is the temperature increase above typical body temperature.

Typical PFA is different from RF ablation in that at least the PF signals generate a temperature change of only a few degrees. PFA typically creates lesions in the patient's tissue sized between about 4 mm to about 6 mm. To create the lesions, a voltage of the PF signal is set to about 900 volts to about 3000 volts. Further, the PF signals are typically generated using particular waveforms.

Typically, during PF signal delivery, the ECG lines are temporarily disconnected from the CARTO™ system PIU such that only noise from a disconnected line is shown. This noise can cover the ECG window and can be distracting to the physician and prevent ECGs collected prior to the disconnection from being seen. Since the CARTO™ system is notified when PF signal delivery will occur, and similarly, when the ECG line disconnect will occur, the CARTO™ system can dim the ECG during the period of disconnect so that the operator is not distracted. When the ECG is reconnected, the CARTO™ system can then return the ECG signal to its full brightness. Alternatively, or in addition thereto, the ECG signal can be shown as 0V or sent to a background display.

Study Overview

This disclosure is more clearly understood with a corresponding study discussed more particularly below with respect to treatment of cardiac arrythmias, such as paroxysmal atrial fibrillation (PAF). The purpose of this study was to establish the overall safety and effectiveness of the catheter 14, in conjunction with generator 50, for the isolation of the atrial pulmonary veins in treatment of subjects with drug refractory, symptomatic, paroxysmal atrial fibrillation using PF/RF energy.

The primary objective of the clinical investigation is to demonstrate safety and effectiveness of the STSF Catheter when used in conjunction with the Generator 50 for Pulmonary Vein Isolation (PVI) in the treatment of subjects with Paroxysmal Atrial Fibrillation (PAF). In particular, the primary objective is to (1) demonstrate safety based on early-onset Primary Adverse Events (PAEs) (within 7 days following the ablation procedure), and (2) demonstrate 12-month effectiveness based on the freedom from documented (symptomatic and asymptomatic) atrial arrhythmia (Atrial Fibrillation (AF), Atrial Tachycardia (AT) or Atrial Flutter (AFL)) episodes based on electrocardiographic data (≥30 seconds on arrhythmia monitoring device) during the effectiveness evaluation period (Day 91-Day 365).

Safety and acute effectiveness will be evaluated through hypothesized primary endpoints and long-term (twelve months or "12M") effectiveness will be evaluated through a hypothesized secondary endpoint. The results of this study provide evidence to support CE-mark registration of these devices. Acute effectiveness means percentage of subjects with acute procedural success, defined as electrical isolation of clinically relevant targeted PVs (confirmed by entrance block) after adenosine/isoproterenol challenge at the end of the index ablation procedure. Use of a non-study device to achieve PVI is considered an acute procedural failure. In addition, subjects who have Catheter 14 inserted but do not undergo ablation due to Study Device (Catheter 14 and Generator 50) related reasons will be considered acute effectiveness failures; subjects who are discontinued due to Non-Study Device related reasons (e.g., pump, other equipment or anatomy that precludes treatment with Catheter 14 and Generator 50 or a commercially available device) will not be considered as acute effectiveness failures.

The primary safety endpoint is the incidence of Primary Adverse Events (PAEs) (within seven (7) days of the index ablation procedure where Catheter 14 and Generator 50 are used per clinical investigation plan). PAEs will include Atrio-Esophageal Fistula, Phrenic Nerve Paralysis (permanent), Cardiac Tamponade/perforation, Pulmonary Vein Stenosis, Device or procedure related death, Stroke/Cerebrovascular Accident (CVA), Major Vascular Access Complication/Bleeding, Thromboembolism, Myocardial Infarction, Transient Ischemic Attack (TIA), Pericarditis, Heart Block, Pulmonary Edema (Respiratory Insufficiency), and Vagal Nerve injury/Gastroparesis. Device or procedure related death, pulmonary vein stenosis and atrio-esophageal fistula that occur greater than one week (7 days) and less than or equal to 90 days post-procedure are considered and analyzed as PAEs.

The additional objectives of this study are to evaluate procedural data, quality of life and the incidence of (procedure and/or device related) serious adverse events during and after procedure up to 12 months.

The study will be carried out as an interventional, prospective, multicenter, single-arm safety and effectiveness evaluation using Catheter 14 in conjunction with the Generator 50.

The study will enroll subjects with drug refractory, symptomatic PAF who are candidates for catheter ablation. Subjects who sign the Informed Consent Form (ICF) and who meet all eligibility criteria will be enrolled and treated with the STSF Catheter and the TRUPULSE™ Generator. A maximum sample size of 135 evaluable subjects is planned in the study. To ensure generalizability of study results, no more than 25% of the total enrollment in the study will be allowed at a single site. All study subjects will be followed-up for 12 months after study procedure.

For the purpose of characterization of safety and to provide an assessment of lesion durability of the investigational ablation system four (4) subsets will be embedded in the study; the Neurological Assessment (NA), a Cardiac Computed Tomography (CT) or Magnetic Resonance Angiogram (MRA) imaging (CT/MRA), an Esophageal Endoscopy evaluation (EE) and a PVI durability subset in a prospective manner. Each subset will consist of 30 subjects, who will undergo the index ablation procedure and additional neurological, PV, esophageal and PVI durability assessments. The same subjects will participate in all four (4) subsets.

All subjects will be evaluated prior to the procedure, prior to discharge, and post procedure at 7 days (Day 7-9), 1 month (Day 23-37), 3 months (Day 76-104), 6 months (Day 166-194), and 12 months (Day 335-379).

Planned statistical analyses of the endpoints and analysis populations of this clinical investigational plan include (1) primary safety endpoint, (2) primary effectiveness endpoint, and (3) secondary effectiveness endpoint. The primary adverse event rate will be compared to a pre-specified threshold of 12% with an assumed true PAE composite rate of 5%.

$$H_0: P_S \geq 0.12 \text{ vs. } H_A: P_S < 0.12,$$

where $P_S$ denotes the rate of primary adverse event.

An exact binomial test of comparing PAE rate against the performance goal of 12% will be performed in the modified Intent To Treat (mITT) analysis set.

The primary effectiveness rate of confirmation of entrance block of all targeted PVs at the end of the index ablation procedure will be compared to a pre-specified threshold of 90% with an assumed true acute effectiveness rate of 97%.

$$H_0: P_E \leq 0.90 \text{ vs. } H_A: P_E > 0.90,$$

where $P_E$ denotes the rate of acute effectiveness success.

An exact binomial test for comparing acute effectiveness success against the performance goal of 90% will be performed in the Per Protocol (PP) analysis set.

The rate of effectiveness success at 12 months, will be compared to a pre-specified threshold of 50% with an assumed true effectiveness rate of 65%.

$$H_0: P_1 \leq 0.50 \text{ vs. } H_A: P_1 > 0.50,$$

where $P_1$ denotes the rate of secondary effectiveness success.

An exact binomial test of comparing 12-month effectiveness success against the performance goal of 50% will be performed in the PP analysis set.

If the study success is met for both primary endpoints, then the secondary hypothesis for comparing the 12-month effectiveness success rate against the performance goal of 50% (with anticipated recurrence-free rate of 65%) will be tested.

A primary endpoint analysis will be performed when all subjects completed their 3-month follow-up. This primary endpoint analysis report will be part of the CE mark application dossier.

Data Monitoring Committee (DMC) will be established to assess clinical safety data on regular intervals and make recommendations on study adaptations, while a Clinical Events Committee (CEC) will adjudicate primary safety endpoint event.

Independent Core Laboratories will conduct objective evaluations of remote arrhythmia monitoring and ECG tracings for presence of atrial arrhythmia and will perform an independent analysis of collected images (Cerebral MRI, Endoscopy, CT/MRA) for evaluation of safety.

The study duration is approximately 17-19 months: 5-7 months for enrollment phase, 3 months for primary endpoint evaluation, and an additional 12 months for effectiveness evaluation. It is understood that data is presented herein for purposes of illustration and should not be construed as limiting the scope of the disclosed technology in any way or excluding any alternative or additional embodiments.

Subjects will arrive at the electrophysiology (EP) laboratory for their ablation procedure and will undergo preparation for the procedure per the hospital's standard protocol (discretion of investigator). The AF Ablation procedure will include (1) anatomical mapping of the Left Atrium (LA), (2) pulmonary Vein (PV) Isolation with PF/RF energy using Catheter 14 and Generator 50, (3) confirmation of PV Isolation (entrance block) with adenosine/isoproterenol challenge, (4) treatment of acute reconnections with additional applications of PF/RF energy, if necessary, and (5) confirmation of entrance block of all targeted PVs at the end of procedure.

In this clinical investigation plan, PF modality is to be used as the primary mode for achieving PVI. Power controlled irrigated RF can be used for the anterior wall and ridge upon investigator discretion. All subjects will undergo PV ablation with the investigational device until PVI is achieved and isolation confirmed via entrance block. If PVI cannot be achieved with the investigational device, a commercial (RF) system, including the RF system employed in this Study can be used to complete the procedure.

A right atrial Cavotricuspid Isthmus (CTI) linear ablation is allowed only in cases with documented typical atrial flutter (AFL) either prior to or during the index ablation procedure. The CTI line cannot be achieved with the investigational device, a commercial (RF) system can be used to complete the procedure.

Safety and acute effectiveness of catheter 14 with generator 50 will be evaluated through primary endpoints and 12-month effectiveness will be evaluated through secondary endpoints. Primary endpoints of the study include (1) demonstrating safety within seven (7) days of the index ablation procedure and (2) demonstrating acute effectiveness (procedural success), defined as electrical isolation of clinically relevant targeted PVs (confirmed by entrance block) after adenosine/isoproterenol challenge at the end of the index ablation procedure. Secondary endpoints include demonstrating 12-month effectiveness, defined as freedom from documented (symptomatic and asymptomatic) atrial arrhythmia episodes (including atrial fibrillation (AF), atrial tachycardia (AT), or atrial flutter (AFL)) based on electrocardiographic data (≥30 seconds on arrhythmia monitoring device) during days 91-365 post-procedure. Acute procedural failure (i.e., failure to achieve entrance block with catheter 14 and generator 50 in any of the clinically relevant targeted PVs) will be deemed a 12-month effectiveness failure.

Additional effectiveness endpoints include PVI durability rate, single procedural success, freedom from documented symptomatic atrial arrhythmia, freedom from documented symptomatic and asymptomatic atrial arrhythmia, use of a non-study device, acute reconnection, repeat ablation procedures, quality of life (QoL), and hospitalization for cardiovascular events.

For PVI durability rate, the study will evaluate (1) the percentage of targeted PVs in the index ablation procedure being durably isolated as confirmed by the electroanatomical mapping 75 days (+/−15 days) post index ablation procedure, and (2) percentage of subjects with durably isolated targeted PVs, as confirmed by the electroanatomical mapping at 75 days (+/−15 days) post index ablation procedure.

For single procedural success, the study will define success as freedom from documented symptomatic atrial arrhythmia (AF, AT or AFL of unknown origin*) episodes based on electrocardiographic data (≥30 seconds on arrhythmia monitoring device) during the effectiveness evaluation period (Day 91-Day 365) following a single index ablation procedure.

For freedom from documented symptomatic atrial arrhythmia (AF, AT or AFL of unknown origin*), the study will evaluate episodes based on electrocardiographic data (≥30 seconds on arrhythmia monitoring device) during the effectiveness evaluation period (Day 91-Day 365). Acute procedure failure will also be considered failure of 12-month symptomatic recurrence free endpoint.

For Freedom from documented (symptomatic and asymptomatic) atrial arrhythmia (AF, AT or AFL of unknown origin*) episodes based on electrocardiographic data (≥30 seconds on arrhythmia monitoring device) during the effectiveness evaluation period (Day 91-Day 365) with extra failure modes will be evaluated. A subject who meets any of the following criteria will also be deemed an effectiveness failure:

Failure to achieve acute procedural success.

Taking a new Antiarrhythmic Drug (AAD) (Class I/Class III) for atrial tachyarrhythmia (AF, AT or AFL of unknown origin*) or taking a previously failed Class I/III AAD at a greater than the highest ineffective historical dose for AF/AFL/AT during the effectiveness evaluation period (Day of 3-month visit—Day 365).

Greater than 1 repeat ablation for AF/AT or AFL of unknown origin in the blanking period or any repeat ablation for AF/AT or AFL of unknown origin* during the effectiveness evaluation period.

The study will also evaluate use of a non-study device for the purpose of either (1) PVI (i.e., touch-up) among all clinically relevant targeted PVs and by subject, or (2) ablation of left atrial non-PV AF targets (i.e., posterior wall) during index ablation procedure or for repeat procedures during blanking period. The term "index ablation procedure" is used herein as a short hand for an ablation procedure where an ablation index (AI) is obtained during the ablation. The ablation is performed by repeated applications of trains of pulses, as described in more detail below. Briefly, the ablation procedure may have approximately 1 second between each repeat application. Each application can calculate and display the AI. In some embodiments, the AI can incrementally increase after each application, in accordance with the calculated Δ AI.

Acute reconnection will be identified by adenosine/isoproterenol challenge among all clinically relevant targeted PVs and by subject.

The study will assess repeat ablation procedures for left atrial arrhythmia (AF, AT or AFL of unknown origin*) within the 12-month FU period to determine (1) percentage of subjects with repeat ablation during blanking period (≤90 days post index ablation procedure); (2) percentage of subjects with repeat ablation after blanking period (Day 91-365 post index ablation procedure); (3) percentage PV reconnection observed during repeat ablation procedures by targeted PVs treated at index ablation procedure and by subject; and (4) percentage of subjects with repeat ablations due to non-PV targets.

The quality of life (QoL) evaluation compares the Atrial Fibrillation Effect on Quality-of-Life (AFEQT™) scores before and at 3, 6 and 12-months after the ablation procedure. Hospitalization for cardiovascular events through 12 months follow-up will be compared to 12 months prior to baseline.

Primary endpoints of the study as to safety include incidence of early onset Primary Adverse Events (PAE) (within 7 days of an ablation procedure which used one or more of the investigational devices). Throughout this disclosure, it is understood that an adverse event (AE) is any untoward medical occurrence in a subject whether or not related to the investigational medical device. FIG. 7 shows a table summarizing intensity or severity of each AE assessed according to classifications. For purposes of this disclosure, an AE can be any undesirable experience (sign, symptom, illness, abnormal laboratory value, or other medical event) occurring to a subject during the course of the study, whether or not it is related to the device or procedure. Physical findings (including vital signs) observed at follow-up, or pre-existing physical findings that worsen compared to baseline, are adverse events if the investigator determines they are clinically significant. As to the study, any medical condition present at the time that the subject is screened is considered as baseline and not reported as an AE. Such conditions should be added to background medical history, if not previously reported. However, if the study subject's condition deteriorates at any time during the study, it can be recorded as an AE.

Similarly, adverse events can be considered if any of the following apply: event is cardiovascular in nature, the event is a serious adverse event, causality is related to investigational device, ablation procedure, or unknown in nature. In contrast, the following clinical events were not considered an adverse event for this study: minor pericarditis attributable to the ablation procedure defined as pleuritic chest discomfort with or without pericardial rub and ECG changes, AF/AFL/AT recurrence requiring pharmacological or synchronized electrical cardioversion during the hospitalization for the index ablation procedure, or throughout the duration of the study. However, new onset of left atrial flutter occurring post-ablation is an AE, and re-ablation for AF or pre-existing AFL/AT itself is not an AE, however any procedural complication is considered an AE and shall be reported within the applicable timelines.

A serious adverse event (SAE) in this disclosure are those considered any event that meets one or more of the following criteria: leads to a death, leads to a serious deterioration in the health of a subject that resulted in a life-threatening illness or injury, a permanent impairment of a body structure or a body function, in-patient hospitalization or prolongation of an existing hospitalization, medical or surgical intervention to prevent life-threatening illness or injury or permanent impairment to body structure or a body function, leads to fetal distress, fetal death or a congenital abnormality or birth defect. It is understood that planned hospitalization for a condition present prior to the subject's enrollment in the study cannot meet the definition of an SAE. An AE would meet the criterion of "hospitalization" if the event necessitated an admission to a health care facility (e.g., an overnight stay). Emergency room visits that do not result in admission to the hospital were evaluated for one of the other serious outcomes. For further reference, FIG. 15 is provided summarizing classifications for the intensity or severity of each AE.

Additional safety endpoints of the study include incidence of Serious Adverse Device Effects (SADEs), incidence of Unanticipated (Serious) Adverse Device Effects (UADEs and USADEs), incidence of Serious Adverse Events (SAEs) within 7 days (early-onset), 8 to 30 days (peri-procedural) and >30 days (late onset) of index ablation procedure, and incidence of non-serious adverse events (non-SAEs).

For neurological assessment (NA), a subset of subjects will represent the neurological assessment (NA) subgroup. Subjects will be assessed for incidences of post-ablation cerebral emboli with either an absence (asymptomatic) or presence (symptomatic) of neurological symptoms. Specifically, an asymptomatic cerebral embolism is defined as an occlusion of a blood vessel in the brain due to an embolus that does not result in any acute clinical symptoms. The presence (symptomatic) or absence (asymptomatic) of neurological symptoms will be determined by the site neurologist of the participating hospitals. The Cerebral MRI data will be analyzed by an independent Core Laboratory.

A total of 30 subjects will be prospectively included in this subset at sites with accessible MRI capabilities and a certified neurologist available to participate in the study. All subjects enrolled in the NA subset will meet all inclusion and exclusion criteria, including the additional exclusion criteria specific for the NA subset.

NA subset subjects will, in addition to the general follow-up schedule, undergo additional assessments including, Cerebral MRI, National Institute of Health Stroke Scale (NIHSS), Modified Rankin Scale (mRS), Mini Mental State Examination (MMSE) and general neurological assessments for evaluation of neurological incidences.

Additional safety endpoints for the neurological assessment subset includes occurrence, anatomical location and size of new post-ablation asymptomatic and symptomatic cerebral emboli observed post-ablation as determined by Magnetic Resonance Imaging (MRI) evaluations, incidence of new or worsening neurological deficits post-ablation and at follow-up, compared to baseline, and a summary of Mini Mental State Examination (MMSE), National Institute of Health Stroke Scale (NIHSS) and Modified Rankin Scale (mRS) at baseline, post-ablation and during follow-up (if lesions were identified in prior evaluation).

For esophageal endoscopy (EE), a subset of study subjects will undergo an esophageal endoscopy within 1 to 3 days post ablation procedure, in addition to the general follow-up schedule, to assess the presence of endoscopically detected thermal esophageal lesions (EDEL) in the region of the contact area between esophagus and LA. The presence or absence of EDEL post ablation will be determined by independent gastroenterologists of the Core Laboratory.

These 30 subjects will be prospectively included by sites with accessible endoscopy capabilities and a certified gastroenterologist available to participate in the study. All subjects who are enrolled in the EE subset will meet all inclusion and exclusion criteria, including the additional exclusion criteria specific for the EE subset.

Additional safety endpoints for the Esophageal Endoscopy Subset will demonstrate occurrence of endoscopically detected esophageal thermal lesions in the region of the contact area between esophagus and left atrium (LA) as determined by post procedure endoscopy An additional subset of study subjects will be enrolled in the cardiac CT/MRA subset and undergo a 3-month CT/MRA in addition to the baseline CT/MRA (all subjects will have a baseline CT/MRA) to assess incidence of post-ablation PV stenosis. A total of 30 subjects will be included in the CT/MRA subset at sites that have the appropriate equipment for CT/MRA imaging.

In addition to this subset, any subjects with signs or symptoms of PV stenosis will undergo a post ablation CT/MRA. These subjects will not be included in the CT/MRA subset analysis. If severe PV stenosis is present, it will be reported as adverse event. The CT/MRA data will be analyzed for PV stenosis by an independent Core Laboratory.

Additional safety endpoints for this subset will demonstrate occurrence of PV stenosis up to 3 months post-ablation as determined by Computed Tomography (CT)/Magnetic Resonance Angiogram (MRA) evaluations.

A subset of 30 study subjects will be enrolled in the PVI Durability subset and will, in addition to the index ablation procedure and general follow up schedule, undergo an electro-anatomical re-map procedure at 75 days (+/−15 days) post index ablation procedure. The re-map is intended to evaluate the durability of the pulmonary vein isolation generated at the index ablation procedure. The assessment of lesion durability will be done by the ablating physician at the participating sites.

Additional procedural endpoints will evaluate data including, but not limited to total procedure time, PVI time, PF/RF application time and mapping time; number of PF/RF applications by left and right PV and by subject; total fluoroscopy time; total study catheter left atrial dwell time; ablation settings used; and use of paralytics and type of anesthesia.

Patient Selection

The criteria for patient selection, methods, personnel, facilities, and training specified in this study were intended to minimize the risk to subjects undergoing this procedure.

Figure 6A:
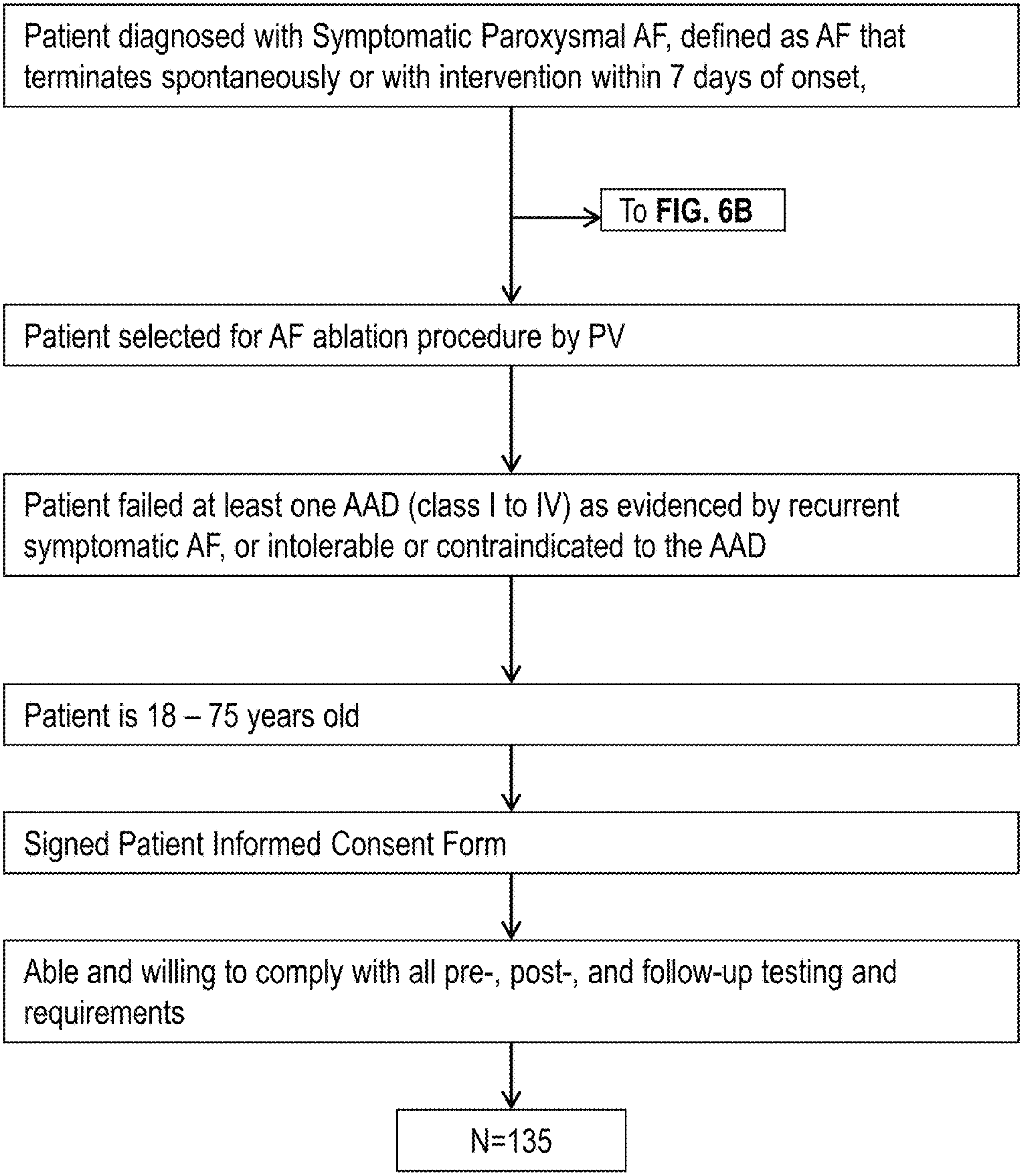
FIG. 6A is a flow chart summarizing inclusion criteria for a study, in accordance with the disclosed technology.
Figure 6B:
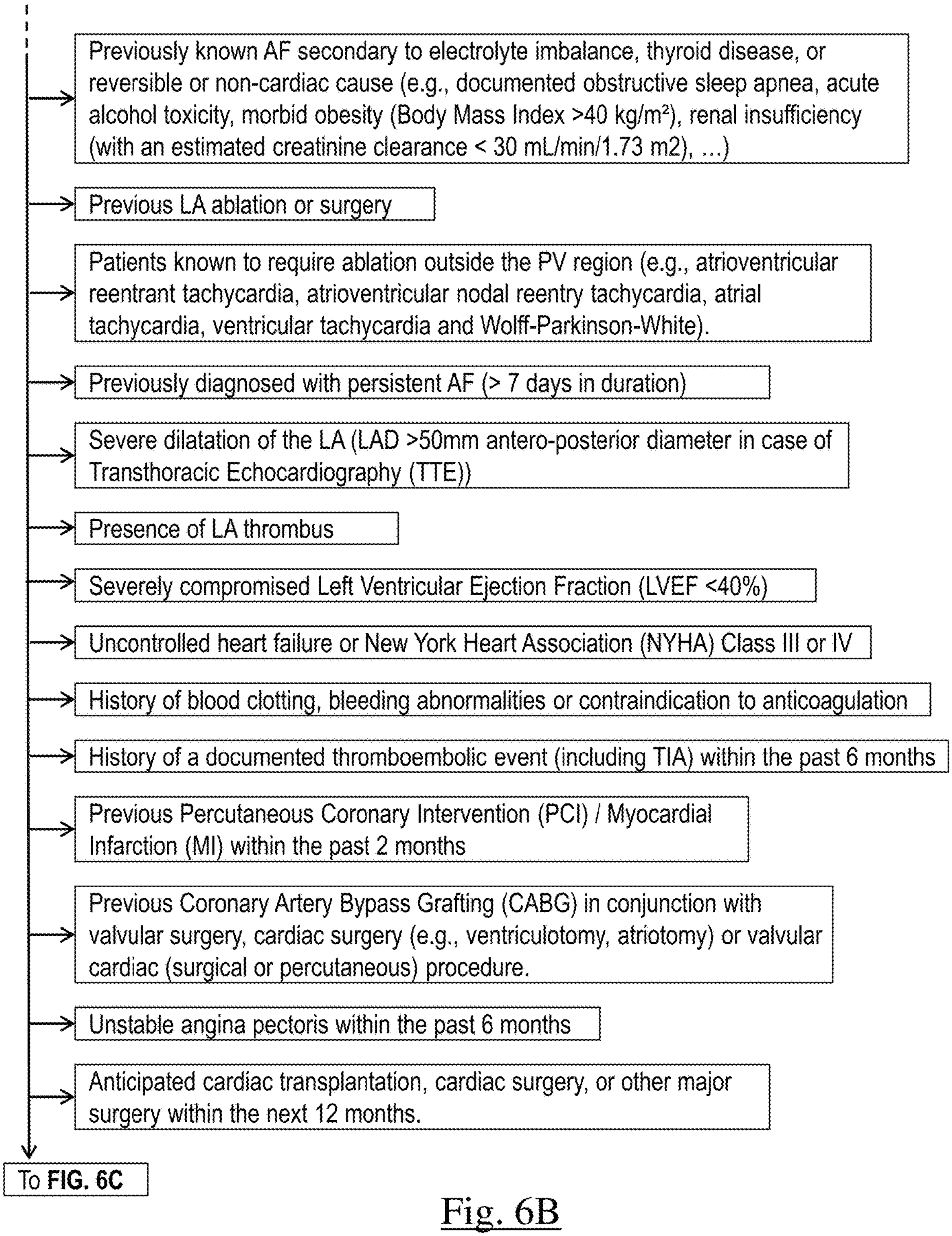
FIGS. 6B and 6C are flow charts summarizing exclusion criteria for a study, in accordance with the disclosed technology.
Figure 6C:
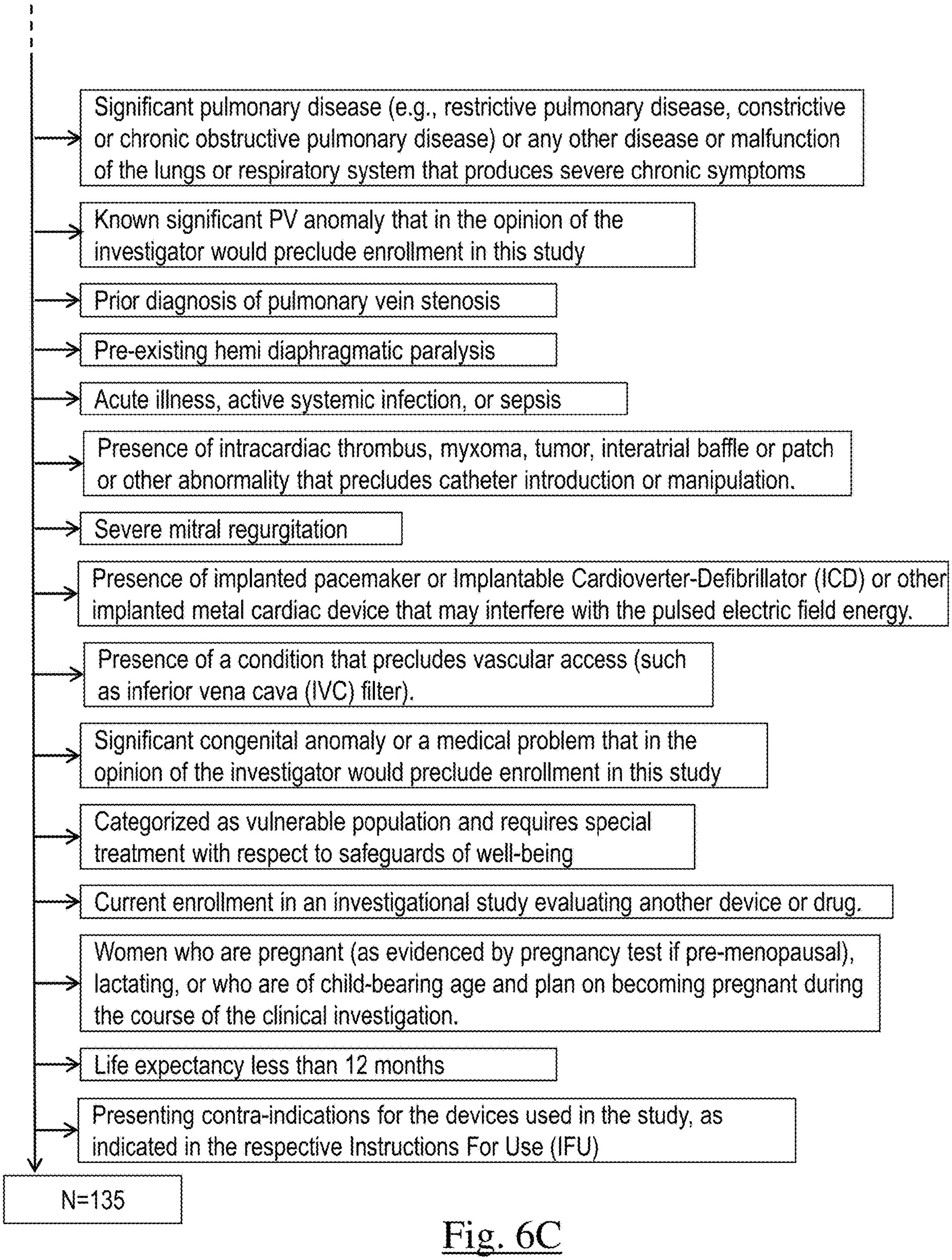

Patients were prescreened carefully prior to enrollment in the study to ensure compliance with the inclusion and exclusion criteria, as shown in FIGS. 6A through 6C. A total of 135 evaluable subjects will be included in the study. Each of the four (4) subsets (NA, CT/MRA, EE and PVI durability) will consist of 30 subjects and will be integrated within the main study.

Inclusion criteria included patients (1) diagnosed with Symptomatic Paroxysmal AF defined as AF that terminates spontaneously or with intervention within 7 days of onset; (2) selected for AF ablation procedure by PVI; (3) that failed at least one AAD (class I to IV) as evidenced by recurrent symptomatic AF, or intolerable or contraindicated to the AAD; (4) between 18-75 years old; (5) willing and capable of providing consent; and (6) able and willing to comply with all pre-, post-, and follow-up testing and requirements.

Exclusion criteria included the following:

1. Previously known AF secondary to electrolyte imbalance, thyroid disease, or reversible or non-cardiac cause (e.g., documented obstructive sleep apnea, acute alcohol toxicity, morbid obesity (Body Mass Index>40 $kg/m^2$), renal insufficiency (with an estimated creatinine clearance<30 mL/min/1.73 m2)).
2. Previous LA ablation or surgery
3. Patients known to require ablation outside the PV region (e.g., atrioventricular reentrant tachycardia, atrioventricular nodal reentry tachycardia, atrial tachycardia, ventricular tachycardia and Wolff-Parkinson-White).
4. Previously diagnosed with persistent AF (>7 days in duration)
5. Severe dilatation of the LA (LAD>50 mm antero-posterior diameter in case of Transthoracic Echocardiography (TTE))
6. Presence of LA thrombus
7. Severely compromised Left Ventricular Ejection Fraction (LVEF<40%)
8. Uncontrolled heart failure or New York Heart Association (NYHA) Class III or IV
9. History of blood clotting, bleeding abnormalities or contraindication to anticoagulation (heparin, warfarin, or dabigatran)
10. History of a documented thromboembolic event (including TIA) within the past 6 months 11. Previous Percutaneous Coronary Intervention (PCI)/Myocardial Infarction (MI) within the past 2 months
12. Previous Coronary Artery Bypass Grafting (CABG) in conjunction with valvular surgery, cardiac surgery (e.g., ventriculotomy, atriotomy) or valvular cardiac (surgical or percutaneous) procedure.
13. Unstable angina pectoris within the past 6 months
14. Anticipated cardiac transplantation, cardiac surgery, or other major surgery within the next 12 months.
15. Significant pulmonary disease (e.g., restrictive pulmonary disease, constrictive or chronic obstructive pulmonary disease) or any other disease or malfunction of the lungs or respiratory system that produces severe chronic symptoms
16. Known significant PV anomaly that in the opinion of the investigator would preclude enrollment in this study.
17. Prior diagnosis of pulmonary vein stenosis
18. Pre-existing hemi diaphragmatic paralysis
19. Acute illness, active systemic infection, or sepsis
20. Presence of intracardiac thrombus, myxoma, tumor, interatrial baffle or patch or other abnormality that precludes catheter introduction or manipulation.
21. Severe mitral regurgitation
22. Presence of implanted pacemaker or Implantable Cardioverter-Defibrillator (ICD) or other implanted metal cardiac device that may interfere with the pulsed electric field energy.
23. Presence of a condition that precludes vascular access (such as inferior vena cava (IVC) filter).
24. Significant congenital anomaly or a medical problem that in the opinion of the investigator would preclude enrollment in this study
25. Categorized as vulnerable population and requires special treatment with respect to safeguards of well-being
26. Current enrollment in an investigational study evaluating another device or drug.
27. Women who are pregnant (as evidenced by pregnancy test if pre-menopausal), lactating, or who are of child-bearing age and plan on becoming pregnant during the course of the clinical investigation.
28. Life expectancy less than 12 months
29. Presenting contra-indications for the devices used in the study, as indicated in the respective Instructions For Use (IFU)

Additional exclusion criteria for Neurological Assessment (NA) subjects included patients with (1) contraindication for MRI such as use of contrast agents due to advanced renal disease, claustrophobia etc. (at PI discretion); (2) presence of iron-containing metal fragments in the body; and (3) unresolved pre-existing neurological deficit. Additional exclusion criteria for Esophageal Endoscopy (EE) subjects included patients with uncontrolled significant gastroesophageal reflux disease (GERD).

In addition to careful screening prior to enrollment, subjects must have a pre-procedure Transesophageal Echocardiogram (TEE) or other imaging technique to screen for the presence of LA thrombus, which is intended to decrease the potential for thromboembolic complications. In accordance with the 2020 ESC AF Management Guidelines, all subjects will be recommended to be maintained on systemic oral anticoagulation therapy for at least two months post-procedure. After two-months post-procedure, a decision regarding continuation of systemic anti-coagulation agents will be based on the patient risk for thromboembolism. Systemic oral anticoagulation will be recommended to be continued beyond two-months post-ablation in patients with $CHA_2DS_2$-VASc score≥2.

In addition, prior to the procedure, anticoagulation therapy should not be interrupted or stopped prior to the procedure (this means no doses should be missed or omitted) and daily regimen should be continued. One dose can be omitted on the evening prior- or day of procedure as per standard of care. AAD therapy and administration of Proton Pump Inhibitors (PPI) should be managed as per the institution's standard of care.

Following the procedure, anticoagulation therapy is strongly recommended for at least 2 months following ablation. Decisions regarding continuation of systemic anticoagulation beyond 2 months post ablation should be based on the subject's stroke risk profile. Per guidance, systemic anticoagulation is recommended to be continued beyond two months post-procedure in subjects with a $CHA_2DS_2$-VASc score of ≥2 (unless deemed contraindicated based on clinical considerations). PPI administration for at least 6 weeks following the procedure is mandatory if an endoscopy is performed post procedure. AAD management during the study will be at the discretion of the investigator. Additional medications needed to treat clinical indications are at the discretion of the clinical investigation physician.

Study Ablation Procedure Guidelines

Generator 50 is capable of controlling the delivery of RF and PF energy to catheter 14. The generator 50 includes a touch screen that allows the user to select the energy type and apply ablations. Before energy delivery it is required to verify if RF or PF is selected on the ablation screen. The start button contains a drag feature. After the start button is dragged or the pedal is pressed, there is a countdown until ablation begins. When the stop button is pressed or the pedal is released, the delivery of energy is terminated. To preform RF ablation, the user selects target power and time from the ablation screen. The user may configure the cutoff temperature and warning temperature from the setup screen.

When used with Catheter 14, a peristaltic irrigation pump (e.g., nGEN™ Pump 60) will deliver a continuous infusion of 2 mL/min of room temperature heparinized saline (lu heparin/1 mL saline) when catheter 14 is in the body. The recommended operating flow settings for Catheter 14 are presented in FIG. 8.

FIGS. 9 and 10 summarizes subject treatment and follow-up schedule for the study, including PV durability, endoscopy, and neurological subsets. The procedure for collecting patient informed consent must be done within 60 days of consent. Medical history, must be collected and documented pre-procedure, and must include, but is not limited to, arrhythmia, AAD therapy failure, heart disease (NYHA), vital signs, $CHA_2DS_2$-VASc Score and thromboembolic events. A pregnancy test must be conducted for all women of childbearing age and potential and must be completed within 72-hours prior to ablation procedure. For left atrium (LA) and left ventricular ejection fraction (LVEF) assessment, imaging must be conducted within 6 months prior to procedure to assess the LA and LVEF, in case the imaging assessment is older than 6 months, LA/LVEF dimensions shall be re-measured during the index ablation procedure prior to insertion of the study catheter. Left atrial thrombus detection must be performed the day before procedure or day of ablation procedure to rule out the presence of atrial thrombus using one of the following modalities TEE, ICE, CT, MRI. Data from 12-lead ECG recordings will be collected (for pre-procedure, can be performed before ICF signature). Arrhythmia monitoring via remote monitoring will be conducted once per week as from 1-month follow-up visit to the end of 5-month follow-up and monthly as of 6-month follow-up visit and whenever subject feels symptoms. Arrhythmia monitoring via 24H Holter will be conducted, site to contact subject and verify if any symptoms experienced during the Holter monitoring. Information on any repeat ablation after the index ablation procedure will be collected. Concomitant medication may include cardiac (i.e., anti-arrhythmia drugs, anticoagulation regimen) & index ablation procedure related (i.e., adenosine, anticoagulation (i.e., heparin, pain medication)). Adverse Events must be collected from the time the subject signs the informed consent onward. Patient questionnaires will only be used in countries with validated languages. For all subjects: CT/MRA to be completed within 6 months prior to the index ablation procedure. Post procedure: for CT/MRA subset to be repeated at 3 month follow-up, for all subjects CT/MRA to be repeated post procedure in case subject presents with PV stenosis symptoms. For PV Durability subset: an electro anatomical map, activation and voltage re-map is to be performed pre and post procedure and to be repeated at 75 days post procedure (+/−15 days). For Endoscopy subset: Endoscopy preferable between 1 day to 3 days (72 hours) post procedure. For procedures on Friday a window of a maximum of 96 hours is justified. If observations are noted on the post-procedure MRI, the subject must have follow-up MRI at the next follow-up visit(s) until observations are resolved. A certified/qualified physician expert must perform neurologic exams at pre- and post-ablation and possibly at other follow-up visits, pending previous findings of micro-emboli/neurologic deficits. For neurological subset subjects, cerebral MRI, neurological exam, NIH stroke scale, mRS, and MMSE must be completed within 72-hours pre-procedure. For procedures on Monday a window of a maximum of 96 hours is justified. Cerebral MRI, neurological exam, and NIH stroke scale pre-discharge must be completed within 72-hours post-procedure. For procedures on Friday a window of a maximum of 96 hours is justified. Full neurological follow-up will be undertaken if neurologic symptoms and/or cerebral ischemic lesions identified in a prior evaluation, specifically at months 1, 3, 6, and 12. If subject returns for a potential study related cardiovascular or neurological visit outside of the CIP-defined visit schedule as deemed required per investigators discretion. Assessments should not be repeated for the study if already done per standard of care within CIP defined time limits.

To predict and control ablation treatment, it is desired to have a universal and linear PFA scale that corresponds to the size of the lesion. For RF ablation, a possible scale can correspond to a size S of a lesion assumed to be proportional to a product of the force F applied by the catheter to the tissue, the power P dissipated during the ablation procedure, and the time T of the procedure. The RF ablation index is described and shown in U.S. Pat. Nos. 7,306,593; 10,517,670; 11,096,741 which are incorporated by reference with a copy provided in the Appendix included with priority application U.S. Patent Application No. 63/496,218. A software product which utilizes this RF ablation index is offered by Biosense Webster as Visitag Surpoint Software Module for use with Biosense Webster catheters and systems. Ablation Index via PFA is described and shown in US Patent Application Publication No. 2021/0186604, which is incorporated by reference with a copy provided in the Appendix included with priority application U.S. Patent Application No. 63/496,218.

Although the possible scale for RF ablation involves power P, the power is fixed per protocol per device. The relation to lesion size for PFA is mainly based on the number of repetitions of the pulses and train of pulses via the pulse generator RMS output current (I) in the following equation: $P=H\cdot I^2$, where H is a constant. This equation applies to all of the discussion for PFA ablation index below.

Thus, a scale to estimate the size S of the lesion according to this assumption can be given using S from an Eq. 1:

$$S = K \cdot F \cdot P \cdot T \quad \text{(Eq. 1)}$$

where K is a constant of proportionality, and $P=H\cdot V_p^2$, where $V_p$ is the PFA pulse generator peak output voltage, and the peak electric field in tissue, $E_p$, is proportional to $V_p$. The proportionality constant depends on the type of catheter, including spacing between electrodes.

As is apparent from Eq. 1, an estimate of the size of a lesion given by the equation is linearly proportional to F, to P, and to T, since, in the equation, each of these variables is raised to the power of one; i.e., from Eq. 1 size S is a linear function of F, of P, and of T. In practice, the estimate of lesion size is incremented after each application i of PFA up to maximum number of applications counted as "i" number of PFA applications (preferably i=24 PFA applications) at each tissue location.

In practice, the relationship between lesion size and F, P, and T is proven to be non-linear, and thus the PFA scale would also be non-linear. Following this observation, the exemplary embodiments of the disclosed invention provide a more exact estimate of the size of a lesion from the values of F, P, and T, with a more exact estimate of lesion size given by finding an integral over time of an expression comprising non-linear functions of F, P, and T. The estimate may be applied during PFA of tissue, separate from estimating the volume of the lesion, the depth of the lesion, and/or the diameter of the lesion produced in the tissue, so as to halt PFA when a desired size is reached.

In an exemplary embodiment of the present invention, a universal PFA linear scale, (named hereinafter "ablation index,"; $AI_{PFA}$ or "PFA AI") is derived by calculating a summation over the time period of a product of the contact force and the number of repetition.

In some exemplary embodiments, PFA AI is provided, which is a summation of the force applied and number of applications of the PFA pulses. The values of the PFA AI (for different size/volume of lesions) are determined experimentally and calibrated. For a given type of cardiac structure and given tissue characteristics, the value of the ablation index is expected to be a repeatable predictor of lesion size. Furthermore, lesion size for a given value of PFA AI may vary due to different structures and tissue characteristics.

The power in PFA is constant. In some embodiments, there is one setting of the power for the alation and the user may not adjust the power parameter. The pulsed field ablation is delivering the power in very short trains of pulses (e.g., <0.5 seconds) and rather than basing the index in part on a power factor defined as a function of time, as in US Pat. Appl. Pub No. US 2021/0186604, which is incorporated herein by reference with a copy provided in the Appendix included with priority application U.S. Patent Application No. 63/496,218, there is provided a discrete ablation index based on the number of applications n. As such, the pulsed field ablation index ($AI_{PFA}$) is defined by the formula in Eq. 2:

$$AI_{PFA} = \sum_{i=0}^{n} [AI_n - AI_{n-1}] \quad \text{(Eq. 2)}$$

where n equals the number of applications of PFA pulses (hereafter referred to as "PFA applications"), has a maximum value of 24, equivalent to the maximum number of pulses, and wherein an Ablation Index for each application of pulses ($AI_n$) is equal to the depth multiplied by a factor A, with the depth being a logarithmic function of force for each application ($force_n$) such that:

$$AI_n = A * (B_n * \ln(\text{force}_n) + C_n) \quad \text{(Eq. 3)}$$

wherein A is a number ranging between 90 and 130 and preferably equal to 110, $B_n$ is a parameter determined by the equation:

$$B_n = B_0 * \ln(n) + B_1 \quad \text{(Eq. 4)}$$

where $B_0$ is equal to approximately 0.2653 and $B_1$ is equal to approximately 0.1623, and $C_n$ is a parameter determined by the equation $$C_n = C_0 * \exp(C_1 * n) \quad \text{(Eq. 5)}$$

where $C_0$ is equal to approximately 0.6862 and $C_1$ is equal to approximately 0.0867.

In some embodiments, $B_1$ and/or $C_n$ may be each independently be set at a constant value for all applications of PFA pulses.

The ablation index from Equation 2 corresponds to one of an estimated volume of a lesion, an estimated depth of the lesion or an estimated diameter of the lesion. In the preferred embodiment, the ablation index provides to the user as a non-dimensional number or range of non-dimensional numbers between a minima and maxima of representing a less than ideal ablation and ideal lesion. In some examples, the ablation index is a non-dimensional scale between 0 and 1000. In other examples, the ablation index is provided as a non-dimensional scale between 250 and 850.

It is intended that the ablation index has the same referential scale whether obtained via the RF ablation index calculation or the PFA ablation index calculation so that ablation index from RF is substantially equivalent to the ablation index obtained from PFA and vice versa. When using catheter 14 for PFA, the ablation index incorporates contact force and number of repetitions (of the pulsed field energy or PFA applications) in a weighted formula to estimate ablation lesion depth and output a predicted ablation index number. Actual ablation index (determined either via RF ablation index calculation or via PFA ablation index calculation) obtained during the actual ablation with PFA or RF can be used to compare with the predicted ablation index (for RF or PFA). Based on the predicted ablation index and how close the correlation with the actual ablation index may be, the physician can decide for or against ablating at a specific location or even to repeat the ablation. In addition, based on the predicted ablation index, the physician can decide if more or less contact force is desired during ablation. The energy generator and associated controller to control RF energy or the PFA pulses, pulse trains or PFA applications are shown and described in US Patent Application Publication No. 2021/0186604, which is hereby incorporated by reference with a copy provided in the Appendix included with priority application U.S. Patent Application No. 63/496,218.

Figure 13:
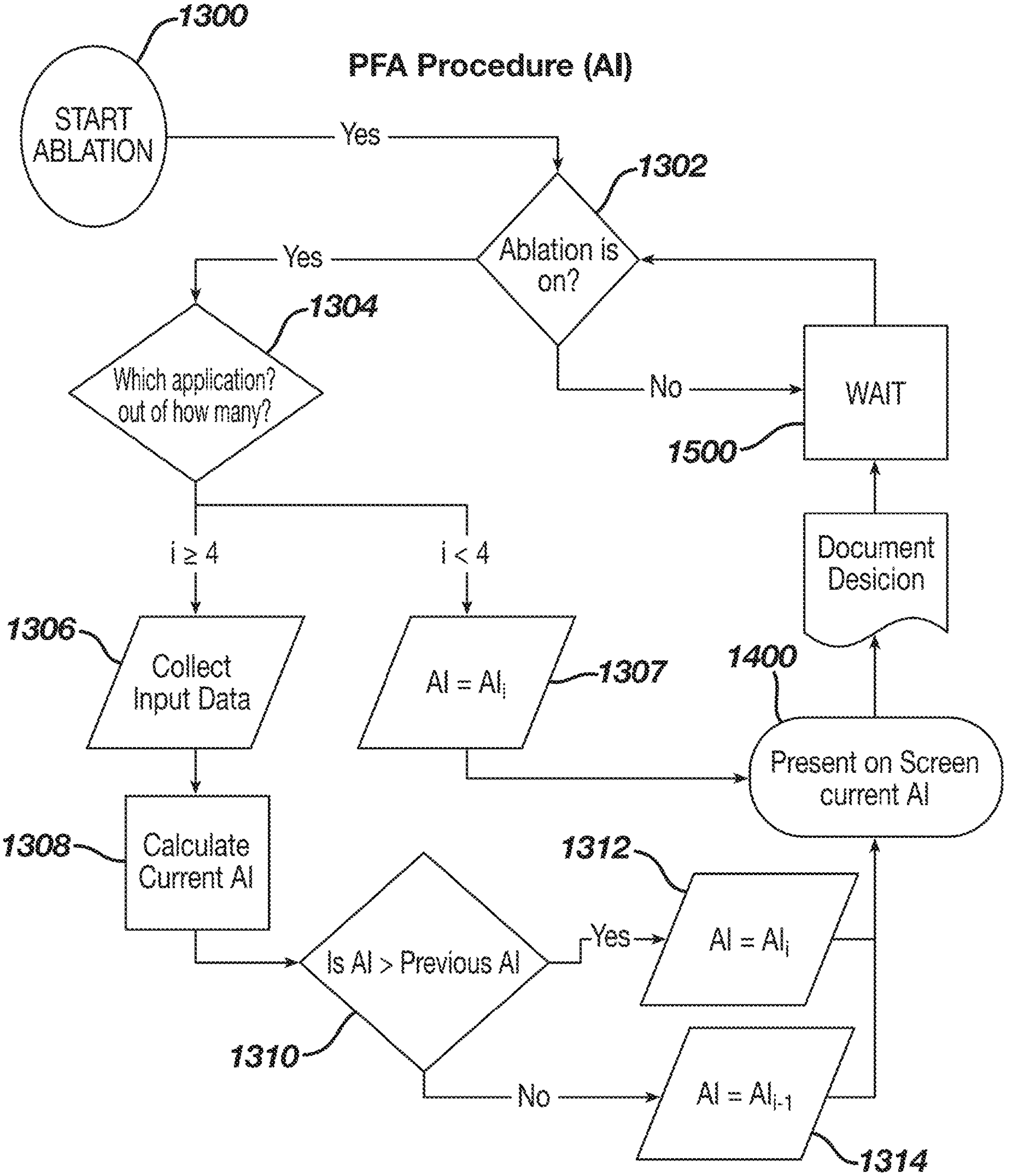
FIG. 13 illustrates an overall flow chart of the ablation index for PFA as utilized for flow chart of FIG. 12, in accordance with the disclosed technology.

The determination of the ablation index (AI) for PFA at each tissue location can be obtained via the flow chart shown in FIG. 13. FIG. 13 is a high level block diagram for determination of the AI. The ablation index for PFA (AI) starts with the Start Ablation command 1300 from the generator monitor. If no ablation is being performed from query 1302, the system moves to a wait state at 1500. On the other hand, if ablation is determined to be ongoing at step 1302, the processor receives the required input data such as the current count or i number of PFA application from the monitor. At step 1302, the processor determines if ablation by PFA is currently being applied via tip electrode 15 to the tissue location. If yes, the processor queries at 1304 as to the current count of PFA applications (with counter "i") being applied via tip electrode 15 at this specific tissue location. The processor queries at step 1307 whether the i number of PFA applications is 4 or greater at this location. If the i number of PFA applications is 4 or greater at this location, then the Ablation Index for this count i of ablation $AI_i$ is calculated at step 1308. A query is made at step 1310 to compare the current AI to the previous AI. In query 1310 if the current AI is greater than previous then the processor sets the AI at step 1312 to be presented to the user as the AI from the current count i of PFA applications. That is, for each application of PFA, the algorithm compares in query 1310 the current result of the AI to the AI of the previous PFA application and chooses the higher value (and in one embodiment, multiplies it by a coefficient of 110). The ablation index (AI) is then presented to the user and stored in the system as $AI_i$. If the query in 1310 that the $AI_i$ is less than or equal to the previous AI, the AI calculated at the one prior (i−1) ablation $AI_{i-1}$ is set at step 1314 to be presented as the current $AI_i$ to the user at step 1400. The AI output is stored in a document file and the system returns to a wait state at 1500.

Returning back to query 1304 of FIG. 13, if the current count i of PFA applications during ablation at each tissue location is less than 4, at step 1307, the processor sets the AI as being the same as the $AI_i$ calculated from the current i number of PFA applications and moves to step 1400 to display the current AI as the AI from the current i number of PFA applications. It is noted that if the current i number of PFA application is less than four at each location, the $AI_i$ of such current count i number of PFA application is, in one embodiment, set to a specified low ablation index number or even zero. It is also noted that the variable $AI_i$ used in a MatLab implementation is the same as variable $AI_I$ discussed for Eq. 3 above.

Figure 11:
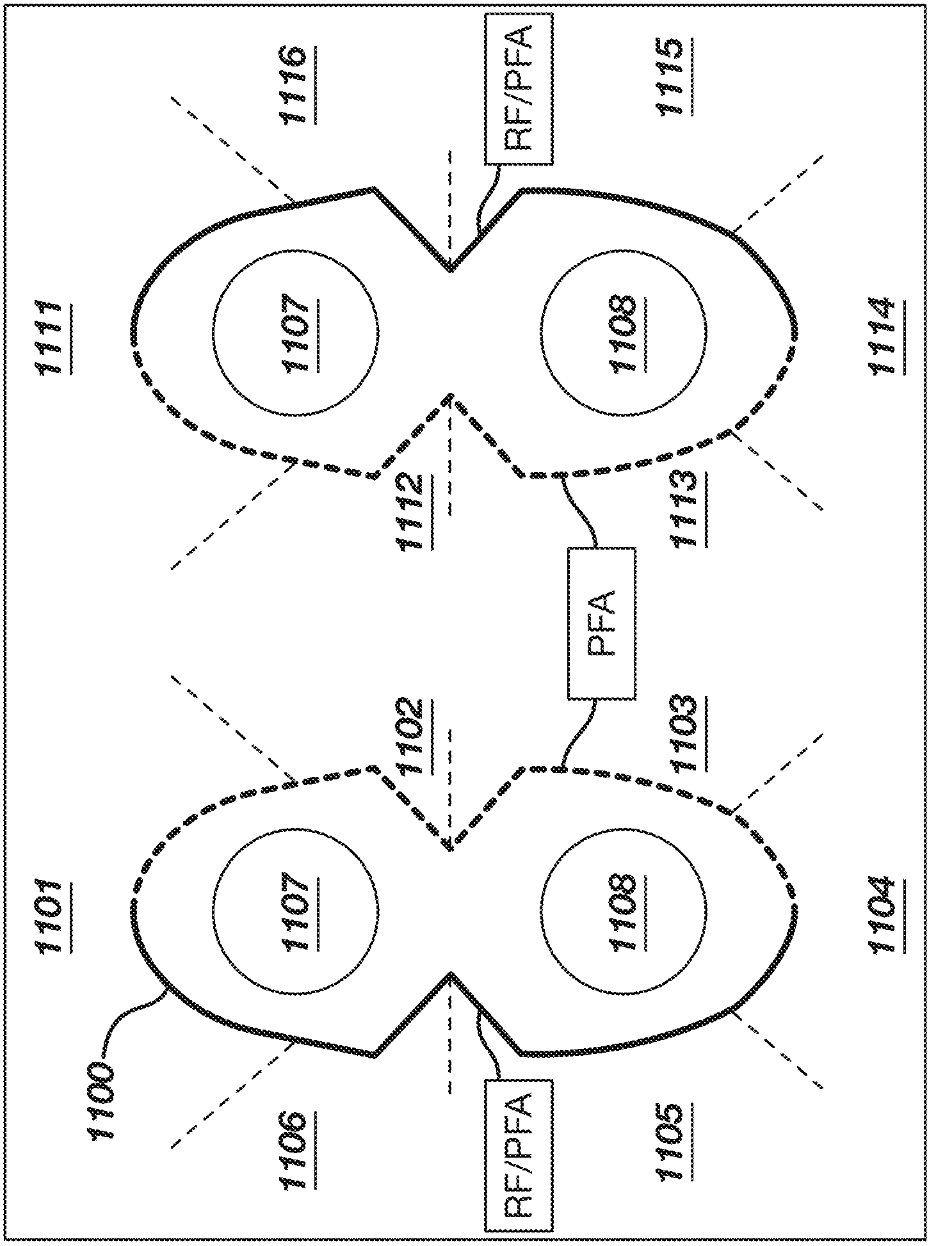
FIG. 11 provides a schematic illustration of VISITAG™ settings for segmenting the left atrium during the procedure of the study, in accordance with the disclosed technology.

FIG. 11 provides an illustration of segments of conduction gaps observed during the ablation index procedure. A first encircling ablation line 1100 is represented by both the thick solid lines and the thick dashed lines. The solid line represent ablation lesions with an ablation index target values≥550 while the dashed line represent ablation index target values≥400 but <550. Conduction gaps can be divided into "residual gaps" and "reconnection gaps" based on their timing and characteristics. Pulmonary vein electrical conduction remaining after an initial anatomical burn is referred to as a "residual gap." Acute reconnections (whether located at residual gaps or elsewhere) detected during the rest of the procedure are named as a "reconnection gaps." Where additional RF energy is applied for touch-up, "success tags" are assigned to the last tag where local PV potential is confirmed to disappear. The two adjacent tags associated with the success tags are termed "gap-related tags." The remaining tags from the first encirclement 1100 are referred to as "non-gap tags." Each PV is divided into six segments (i.e. roof, superior anterior, inferior anterior, superior posterior, inferior posterior, and inferior) for subsequent analyses. Including two additional areas near the esophagus and otherwise unclassified regions, a total of 16 segments were assigned by CARTO™ operators, including the following:

LRF, left roof 1101;

LSPST, left superior posterior 1102;

LIPST, left inferior posterior 1103;

LINF, left inferior 1104;

LIANT, left anterior 1105;

LSANT, left superior anterior 1106;

LSPV, left superior pulmonary vein 1107;

LIPV, left inferior pulmonary vein 1108;

RRF, right roof 1111;

RSPST, right superior posterior 1112;

RIPST, right inferior posterior 1113;

RINF, right inferior 1114;

RIANT, right anterior 1115;

RSANT, right superior anterior 1116;

RSPV, right superior pulmonary vein 1117;

RIPV, right inferior pulmonary vein 1118;

Subjects will arrive to the electrophysiology (EP) laboratory for their ablation procedure and will undergo preparation for the procedure per the hospital's standard protocol (discretion of investigator), including the following:

Anesthesia or sedation should be delivered per standard EP lab procedure. It is highly recommended to ensure presence of an anesthesiologist during the procedures.

Placement of two indifferent electrodes on the patient prior to mapping.

Esophageal monitoring/localization (investigator discretion) with CARTOSOUND® and/or ICE, barium swallow or temperature probe.

CARTO™ Respiratory gating recommended (unless using Jet Ventilation).

Introduce an Intracardiac Echo (ICE) probe to review LA anatomy and PVs (at investigator discretion).

Diagnostic catheter placement in either (1) Coronary sinus catheter in the CS for pacing purposes is recommended or (2) Other catheters may be placed at the discretion of investigator Administration of heparin bolus prior to or immediately following transseptal puncture.

A double or single transseptal puncture should be performed per standard EP lab (at the discretion of the investigator).

Cardioversion if subject is in AF (at discretion of investigator).

After preparation, subjects will undergo mapping prior to the ablation procedure. Mapping will include the following:

Creation of a left atrial anatomical map, including PV anatomy prior to ablation, utilizing a multi-electrode mapping catheter.

Additional imaging techniques such as 3D rotational angio (at investigator discretion), or CT integration can be used to supplement the map.

A pre-ablation paced activation and bi-polar voltage map may be created at physician discretion and if SOC.

For subjects participating in PVI durability subset, creation of paced activation map and bipolar voltage map, utilizing a multi-electrode mapping catheter.

Pace the phrenic nerve prior to ablation in the region of the right sided PV's in order to evaluate the proximity. NOTE: in case of deep sedation a fluoroscopic evaluation of the diaphragm may be used.

The ablation procedure will include the following steps:

Confirmation of ACT≥300 seconds prior to start ablation with investigational catheter and systematic anticoagulation with heparin should be administrated. ACT must be targeted to be maintained ≥300 seconds throughout the ablation. ACT level must be checked on regular basis while investigational device is in the left atrium. If ACT is below 300 seconds, systematic anticoagulation with heparin should be administrated to ensure an ACT target of 300 seconds without pausing ablation procedure.

Introduce the compatible 8.5 Fr or greater sheath, if not used for mapping. Before inserting the sheath into the patient, flush the sheath with heparinized normal saline to remove air bubbles.

Introduce Catheter 14 as per Instructions for use (IFU).

When position is satisfactory, commence energy delivery with the investigational catheter per recommended workflow.

For subjects undergoing pulmonary vein isolation, the procedure further requires the following:

Use point-by-point ablation to obtain a contiguous lesion set for ipsilateral PV isolation.

Create VISITAG™ settings in order to segment the left atrium during the procedure according to the image in FIG. 11.

Use the ablation parameters, and VISITAG™ targets as recommended by IFU and per physician training.

Evaluate the Inter-tag Distance (ITD) using the VISITAG™ Module distance tool. An ITD of ≤6 mm is recommended.

Prepare 1-2 mg nitroglycerine for either intravenous or intracoronary administration to limit/reduce coronary spasm when ablating near the coronary artery.

All subjects will undergo PV ablation with the investigational device until PVI is achieved in all targeted PV's, including PF is recommended to be used as the primary ablation modality for achieving PVI Power controlled irrigated RF can be used for the anterior wall and ridge upon clinical judgement and per investigator discretion.

ONLY after investigator deems unable to achieve PVI with the investigational device, a commercial (RF) system can be used to complete the procedure (PVI only).

Confirmation of entrance block (exit block is optional) (PVI) of all clinically relevant targeted PVs To verify entrance block, analyze electrograms in coronary sinus and/or atrial paced rhythm to confirm that no PV potentials are present.

After pulmonary vein isolation, the procedure includes the following steps:

Administer adenosine/isoproterenol for each clinically relevant targeted PV to rule out dormant conduction.

If any, treat reconnected PV regions by reviewing remaining signals on reconnection location and deliver energy in corresponding locations. As per above recommendation, PF is the primary modality, but RF can be used based on clinical judgement.

Confirm and document of final entrance block (exit block is optional) (PVI) of all clinically relevant targeted PVs

- To verify entrance block, analyze electrograms in coronary sinus and/or atrial paced rhythm to confirm that no PV potentials are present.
- Use a multi-electrode mapping catheter for confirmation per investigators choice The ablation procedure is considered complete when confirmation of entrance block in all clinically relevant targeted PVs is confirmed.

After last application or confirmation of final entrance block (exit block is optional) at the right sided PVs, evaluate diaphragmatic capture while pacing the phrenic nerve. NOTE: in case of deep sedation a fluoroscopic evaluation of the diaphragm might be used.

A post paced activation and bipolar voltage map may be created at physician discretion and if SOC.

For subjects participating in PVI durability subset:

- creation of paced activation map and bipolar voltage map, utilizing the same multi-electrode mapping catheter as pre-procedure.

For ablation outside the PV region, a right atrial CTI linear ablation is allowed only in cases with documented typical atrial flutter identified either prior to or during the procedure. The investigational system, Catheter 14 with generator 50 in RF and/or PF mode should be used based upon investigator decision. If block of CTI line cannot be achieved with the investigational system, a commercially approved RF catheter with a compatible commercially available RF generator may be used. Prophylactic ablation outside the PV region (in example SVC, PW, roofline) is not allowed in the study.

If an arrhythmia is requiring ablations outside the PV or CTI line, the operator must complete the following:

- Prior to insertion of Catheter 14 (consistent with exclusion criteria) investigators will be required to switch to the commercial setup using a commercially available catheter used with a commercially available RF generator. The subject will be considered a screen failure (<ICF signature) or excluded from the study (>ICF signature).
- After insertion of Catheter 14, the subject will undergo PVI and/or CTI line with study set up followed by commercial RF therapy to complete the procedure (treatment of arrhythmia outside PV region). The subject will be evaluable for acute success but excluded from the 12-month effectiveness cohort and followed till 3-months post procedure. Ongoing AE(s) at month 3 shall be followed up until resolution (with or without sequelae)

Results of the Study

During the study, investigators collected data including, but not limited to: number of PF/RF applications, energy delivered, PF/RF application time, ablation settings used, contact force values, actual ablation index, predicted ablation index, lesion size, lesion volume, correlation between predicted lesion and effectiveness rate of pulmonary vein isolation for each patient (and groups of patients) as well as the use of a non-study catheter for PVI, number of PF/RF applications per left and right PV per left and right PV, number of PF/RF applications per target PV and by subject, number of PF/RF applications required with a non-study catheter, PVI confirmed with multi-electrode mapping catheter, PV acute reconnection (early or dormant), procedure time (from first femoral puncture to last catheter out), mapping time (start mapping-end mapping), total fluoroscopy time, total study catheter LA dwell time (from first study catheter insertion in LA until study catheter removal from LA), ECG data, total fluid delivered via study catheter, total fluid delivered via intravenous line (if captured), fluid output (if captured), device deficiency information (if applicable), procedural medication (paralytics), use of paralytics and type of anesthesia, and the like.

Figure 12:
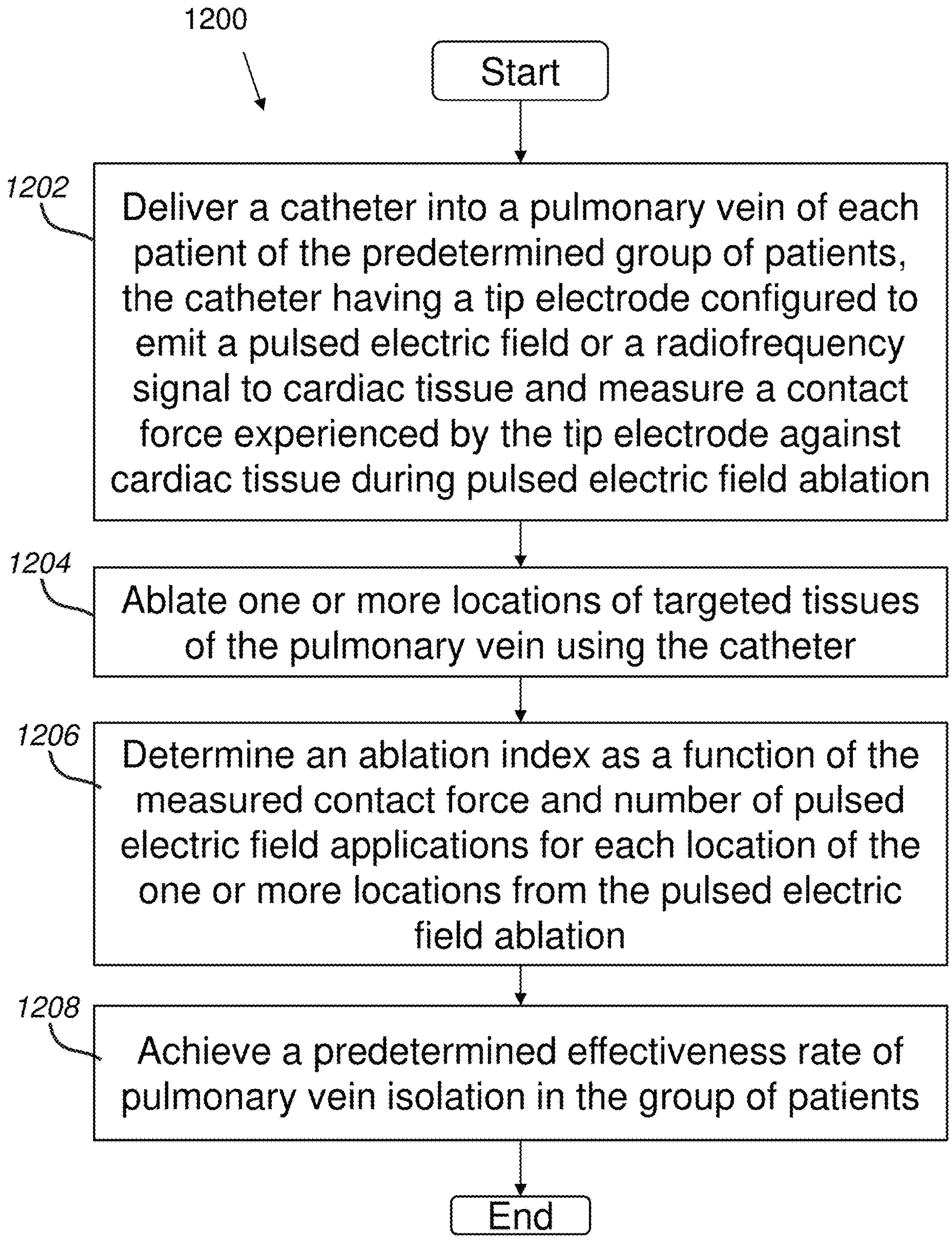
FIG. 12 illustrates a flowchart of a method for treating atrial fibrillation in a group of patients using RF energy and PFA energy, in accordance with the disclosed technology.

FIG. 12 illustrates an example of a method 1200 of treating atrial fibrillation in a predetermined group of patients meeting predetermined inclusion and exclusion criteria. The method 1200 can include delivering a catheter 14 into a pulmonary vein of each patient of the predetermined group of patients, the catheter 14 having a tip electrode configured to emit a pulsed electric field or a radiofrequency signal to cardiac tissue and measure a contact force experienced by the tip electrode against cardiac tissue during pulsed electric field ablation (Step 1202). Once in contact, the method 1200 can include ablating one or more locations of targeted tissues of the pulmonary vein using the catheter 14 (Step 1204). After ablating targeted tissues, the method 1200 can include determining an ablation index AI (from FIG. 13) as a function of the measured contact force and number of pulsed electric field applications for each location of the one or more locations from the pulsed electric field ablation (Step 1206). After ablating targeted tissues, the method 1200 can further include achieving a predetermined effectiveness rate of pulmonary vein isolation in the group of patients within an effectiveness evaluation period (Step 1208).

In some examples, method 1200 can further include applying, to the targeted tissue, a first ablation signal comprising forming a first lesion comprising a first size with little or no first temperature change in a temperature of the targeted tissue. In one example, the first ablation signal can be the RF ablation signal. However, in other examples, the PF ablation signal can be the first ablation signal. The first ablation signal can form a first lesion comprising a first size and generate a first temperature change in the tissue. A second ablation signal can be applied to the tissue with the electrode to form a second lesion in the tissue. In the example, the second ablation signal can be different from the first ablation signal. The second lesion can be formed with a second size. The second ablation signal can generate a second temperature change in the tissue different from the first temperature change by at least 10° C. As above, if the RF signal is the first signal, the PFA signal can be the second signal. Where RF ablation causes tissue temperature changes greater than 20° C., the PFA causes a temperature change of just a few degrees.

Alternately a first lesion can be formed with little or no first temperature change in a temperature of the tissue and a second lesion can be formed by generating a second temperature change in the tissue different from the first temperature change by at least 10° C.

Although not depicted, method 1200 can include forming a combined lesion which can result from applying the first ablation signal and the second ablation signal. The deeper/larger combined lesion can be formed from the combination of the first lesion and the second lesion having a combined size. The combined size can be about 20% to about 40% greater than either of the first size and the second size. The ablation signals can be applied sequentially. This can include first applying the RF signal and then applying the PF signal or visa-a-versa. However, given that the RF signals can be generated using alternating current (AC) and the PF signals can be generated using very short pulses of direct current (DC), another example can have both signals generated at the same time or at least having some overlap of application of the RF and PF signals. Additionally, contact force between the tissue and the electrode is known to be a factor in the effectiveness of creating a lesion. In one example the contact force can be about 5 grams to about 40 grams.

An ablation system for electrophysiology uses can have an alternating current (AC) signal generator configured to provide radiofrequency signals at high power and a direct current (DC) signal generator configured to provide very short duration with high voltage pulses. The system also includes a catheter having an end effector electrically coupled to the AC signal generator and the DC signal generator. The end effector can have at least one electrode disposed on the end effector so that the electrode delivers the high voltage pulses from the at least one electrode to organ tissue inside a patient to first and second return electrodes coupled to the outside body of the patient and deliver the RF signal between the at least one electrode to one of the first or second return electrodes. The RF signals and the high voltage pulses can be applied either sequentially or simultaneously to the organ tissue.

In an example, the end effector can have a cylindrical member with a distal tip electrode and irrigation ports disposed on the cylindrical member to provide irrigation fluid proximate the distal tip electrode.

Another example can have the distal tip electrode coupled to a force sensor. Further, the radiofrequency signals can be applied with a contact force of approximately 5 grams or more. Also, the radiofrequency signals can be provided having at least 25 Watts of power. The radiofrequency signals can also include a frequency from 350 kHZ to about 500 kHZ and the radiofrequency signals can be provided for a duration of at least 1 second.

For other examples, the high voltage pulses can include an amplitude of at least 800 V. In addition, a duration of each of the high voltage pulse can be less than 20 microseconds and provide a pulse train of approximately 100 microseconds. A time gap of any value selected from 0.3 to 1000 milliseconds can be provided between adjacent pulse trains. These pulse trains can provide a PFA burst. The PFA burst can have any value from 2 to 100 pulse trains with a duration of the PFA burst comprising any value selected from zero to 500 milliseconds. Furthermore, the high voltage pulse can provide approximately 60 Joules or less.

As will be appreciated, method 1200 described herein can be varied in accordance with the various elements and examples described herein. That is, methods in accordance with the disclosed technology can include all or some of the steps described above and/or can include additional steps not expressly disclosed above. Further, methods in accordance with the disclosed technology can include some, but not all, of a particular step described above. Further still, various methods described herein can be combined in full or in part.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. But other equivalent methods or compositions to these described aspects are also contemplated by the teachings herein. Therefore, the present disclosure should not be limited to any single aspect, but rather construed in breadth and scope in accordance with the appended claims.

The disclosed technology described herein can be further understood according to the following clauses:

Clause 1: A method of treating atrial fibrillation in a predetermined group of patients meeting predetermined inclusion and exclusion criteria, the method comprising: delivering a catheter into a pulmonary vein of each patient of the predetermined group of patients, the catheter having a tip electrode configured to emit either a pulsed electric field or a radiofrequency signal to cardiac tissue and measure a contact force experienced by the tip electrode against cardiac tissue during pulsed electric field ablation; ablating one or more locations of targeted tissues of the pulmonary vein using the catheter; determining an ablation index as a function of the measured contact force and number of pulsed electric field applications for each location of the one or more locations from the pulsed electric field ablation; and achieving a predetermined effectiveness rate of pulmonary vein isolation in the group of patients within an effectiveness evaluation period.

Clause 2: The method of Clause 1, wherein determining an ablation index for pulsed field ablation comprises calculating the pulsed field ablation index $$AI_{PFA} \text{ with: } AI_{PFA} = \sum_{i=0}^{n}[AI_n - AI_{n-1}],$$

where n is the number of applications of pulsed electric field applications and $AI_n$ is an index for each application of pulses and is defined by the formula: $AI_n = A*(B_n*\ln(force_n)+C_n)$, where A is a number ranging between 90 and 130, $B_n$ is a parameter determined by the formula: $B_n = B_0*\ln(n)+B_1$, and $C_n$ is a parameter determined by the formula: $C_n = C_0*\exp(C_1*n)$.

Clause 3: The method of Clause 2, wherein $B_0$ is equal to approximately 0.2653 and $B_1$ is equal to approximately 0.1623, and $C_0$ is equal to approximately 0.6862 and $C_1$ is equal to approximately 0.0867.

Clause 4: The method of any of Clauses 1-3, wherein the ablation index corresponds to an estimated volume of a lesion.

Clause 5: The method of any of Clauses 1-4, wherein the ablation index corresponds to an estimated depth of the lesion.

Clause 6: The method of any of Clauses 1-5, wherein the ablation index corresponds to an estimated diameter of the lesion.

Clause 7: The method of any of Clauses 1-6, wherein the predetermined effectiveness rate is defined by a freedom from documented atrial fibrillation, atrial tachycardia, or atypical atrial flutter episodes based on electrocardiographic data through the effectiveness evaluation period.

Clause 8: The method of any of Clauses 1-7, wherein the predetermined effectiveness rate is defined by an average number of pulsed electric field (PF) applications per patient and contact force required to isolate all pulmonary veins.

Clause 9: The method of any of Clauses 1-8, wherein the predetermined effectiveness rate includes complication rates of 10% or less and is defined by existence or non-existence of asymptomatic cerebral embolic lesions at a discharge magnetic resonance imaging (MRI).

Clause 10: The method of any of Clauses 1-8, wherein the predetermined effectiveness rate includes complication rates of 8% or less and is defined by existence or non-existence of asymptomatic cerebral embolic lesions at a discharge magnetic resonance imaging (MRI).

Clause 11: The method of any of Clauses 1-8, wherein the predetermined effectiveness rate includes complication rates of 6% or less and is defined by existence or non-existence of asymptomatic cerebral embolic lesions at a discharge magnetic resonance imaging (MRI).

Clause 12: The method of any of Clauses 1-8, wherein the predetermined effectiveness rate includes complication rates of 5% or less and is defined by existence or non-existence of asymptomatic cerebral embolic lesions at a discharge magnetic resonance imaging (MRI).

Clause 13: The method of any of Clauses 1-8, wherein the predetermined effectiveness rate includes complication rates range from about 10% to about 1% and is defined by existence or non-existence of asymptomatic cerebral embolic lesions at a discharge magnetic resonance imaging (MRI).

Clause 14: The method of any of Clauses 1-13, wherein the predetermined effectiveness rate includes complication rates of approximately 0% and is defined by existence or non-existence of esophageal injury erythema.

Clause 15: The method of any of Clauses 1-14, wherein the predetermined effectiveness rate is approximately 100% and is defined by electrically isolating all targeted pulmonary veins without use of a focal ablation catheter.

Clause 16: The method of any of Clauses 1-14, wherein the predetermined effectiveness rate is approximately 98% and is defined by electrically isolating all targeted pulmonary veins without use of a focal ablation catheter.

Clause 17: The method of any of Clauses 1-14, wherein the predetermined effectiveness rate is approximately 96% and is defined by electrically isolating all targeted pulmonary veins without use of a focal ablation catheter.

Clause 18: The method of any of Clauses 1-14, wherein the predetermined effectiveness rate is approximately 94% and is defined by electrically isolating all targeted pulmonary veins without use of a focal ablation catheter.

Clause 19: The method of any of Clauses 1-14, wherein the predetermined effectiveness rate is approximately 92% and is defined by electrically isolating all targeted pulmonary veins without use of a focal ablation catheter.

Clause 20: The method of any of Clauses 1-19, wherein the predetermined effectiveness rate is defined by pulmonary vein isolation touch-up by a focal catheter among all targeted pulmonary veins.

Clause 21: The method of any of Clauses 1-20, wherein the predetermined effectiveness rate is defined by using focal catheter ablation for non-PV triggers during the pulmonary vein isolation.

Clause 22: The method of any of Clauses 1-21, wherein the predetermined effectiveness rate comprises a long-term effectiveness rate.

Clause 23: The method of any of Clauses 1-22, wherein the predetermined effectiveness rate is defined by an average number of radio frequency (RF) applications per vein and RF time required to isolate all pulmonary veins.

Clause 24: The method of any of Clauses 1-23, wherein the predetermined effectiveness rate is defined by an average number of RF applications per vein and RF time required to isolate common pulmonary veins.

Clause 25: The method of any of Clauses 1-24, wherein the predetermined effectiveness rate is defined by an average number of RF applications per patient and RF time required to isolate common pulmonary veins.

Clause 26: The method of any of Clauses 1-25, wherein the predetermined effectiveness rate is defined by determining incidence of complication rates being 10% or less of post-ablation symptomatic and asymptomatic cerebral emboli as compared to pre-ablation.

Clause 27: The method of any of Clauses 1-25, wherein the predetermined effectiveness rate is defined by determining incidence of complication rates being 8% or less of post-ablation symptomatic and asymptomatic cerebral emboli as compared to pre-ablation.

Clause 28: The method of any of Clauses 1-25, wherein the predetermined effectiveness rate is defined by determining incidence of complication rates being 5% or less of post-ablation symptomatic and asymptomatic cerebral emboli as compared to pre-ablation.

Clause 29: The method of any of Clauses 1-25, wherein the predetermined effectiveness rate is defined by determining incidence of complication rates ranging from about 8% to about 1% of post-ablation symptomatic and asymptomatic cerebral emboli as compared to pre-ablation.

Clause 30: The method of any of Clauses 1-29, wherein the effectiveness evaluation period is approximately seven days.

Clause 31: The method of any of Clauses 1-29, wherein the effectiveness evaluation period is approximately three months.

Clause 32: The method of any of Clauses 1-29, wherein the effectiveness evaluation period is approximately twelve months.

Clause 33: The method of Clause 1, further comprising: achieving, by the catheter, an effectiveness rate of pulmonary vein isolation in approximately 97% of subjects in the group of patients within seven days of successful pulmonary vein isolation.

Clause 34: The method of Clause 1, further comprising: achieving, by the catheter, an effectiveness rate of pulmonary vein isolation in approximately 96% of subjects in the group of patients within seven days of successful pulmonary vein isolation.

Clause 35: The method of Clause 1, further comprising: achieving, by the catheter, an effectiveness rate of pulmonary vein isolation in approximately 95% of subjects in the group of patients within seven days of successful pulmonary vein isolation.

Clause 36: The method of Clause 1, further comprising: achieving, by the catheter, an effectiveness rate of pulmonary vein isolation in approximately 94% of subjects in the group of patients within seven days of successful pulmonary vein isolation.

Clause 37: The method of Clause 1, further comprising: achieving, by the catheter, an effectiveness rate of pulmonary vein isolation in approximately 65% of subjects in the group of patients within twelve months after atrial fibrillation.

Clause 38: The method of Clause 1, further comprising: achieving, by the catheter, pulmonary vein isolation and at least a 97% safety endpoint within seven days of successful pulmonary vein isolation.

Clause 39: The method of Clause 1, further comprising: achieving, by the catheter, pulmonary vein isolation and at least a 96% safety endpoint within seven days of successful pulmonary vein isolation.

Clause 40: The method of Clause 1, further comprising: achieving, by the catheter, pulmonary vein isolation and at least a 95% safety endpoint within seven days of successful pulmonary vein isolation.

Clause 41: The method of Clause 1, further comprising: achieving, by the catheter, pulmonary vein isolation and at least a 94% safety endpoint within seven days of successful pulmonary vein isolation.

Clause 42: The method of any of Clauses 1-41, wherein the delivering step comprises applying a contact force between the one or more targeted tissue and the catheter of about 5 grams to about 40 grams.

Clause 43: The method of any of Clauses 1-42, further comprising: setting a power of the RF signal to about 1 Watt to about 400 Watt; maintaining the RF signal for about 1 second to about 60 seconds; and generating, at the one or more locations of targeted tissues, a temperature change from about 20° C. to about 70° C.

Clause 44: The method of any of Clauses 1-43, further comprising: setting a voltage of the PF signal to about 900 volts to about 3000 volts.

Clause 45: The method of any of Clauses 1-44, wherein the RF signal forms a lesion comprising a size between about 3 mm to about 5 mm.

Clause 46: The method of any of Clauses 1-45, wherein the PF signal forms a lesion comprising a size between about 4 mm to about 6 mm.

Clause 47: The method of any of Clauses 1-46, further comprising: temporarily dimming a brightness level, during pulsed electric field ablation, of a visual representation of a tissue signal emitted from a respective body in the group of patients from a first brightness level to a second brightness level; and after pulsed electric field ablation, returning the visual representation of the signal emitted from the respective body in the group of patients to the first brightness level.

Clause 48: The method of any of Clauses 1-46, further comprising: temporarily displaying, during pulsed electric field ablation, the signal emitted from the respective body in the group of patients to as indicia representative of 0V during pulsed electric field ablation.

Clause 49: A system for applying pulsed field ablation to treat atrial fibrillation in a group of patients, the system comprising: a catheter comprising a tip electrode configured to emit a pulsed electric field or a radiofrequency signal to cardiac tissue and ablate one or more locations of cardiac tissue of the pulmonary vein; and a processor configured to: measure a contact force experienced by the tip electrode against cardiac tissue during pulsed electric field ablation, and determine a pulsed field ablation index as a function of the measured contact force and number of pulsed electric field applications for each location of the one or more locations, wherein the system is configured to achieve a predetermined effectiveness rate of pulmonary vein isolation in the group of patients within an effectiveness evaluation period.

Clause 50: The system of Clause 49, wherein the processor is further configured to calculate the pulsed field ablation index defined by the formula:

$$AI_{PFA} = \sum_{i=0}^{n} [AI_n - AI_{n-1}],$$

where n is the number of applications of pulsed electric field applications and $AI_n$ is an index for each application of pulses and is defined by the formula: $AI_n = A*(B_n*\ln(force_n)+C_n)$, where A is a number ranging between 90 and 130, $B_n$ is a parameter determined by the formula: $B_n = B_0*\ln(n)+B_1$, and $C_n$ is a parameter determined by the formula: $C_n = C_0*\exp(C_1*n)$.

Clause 51: The system of Clause 50, wherein $B_0$ is equal to approximately 0.2653 and $B_1$ is equal to approximately 0.1623, and $C_0$ is equal to approximately 0.6862 and $C_1$ is equal to approximately 0.0867.

Clause 52: The system of any of Clauses 49-51, wherein the processor is further configured cease application of the pulsed field ablation applications in response to the calculated pulsed field ablation index reaching a prespecified target ablation index value.

Clause 53: The system of Clause 52, wherein the processor is further configured to present the pulsed field ablation index and the prespecified target ablation index value to a user.

Clause 54: The system of any of Clauses 49-53, wherein the ablation index corresponds to an estimated volume of a lesion.

Clause 55: The system of any of Clauses 49-54, wherein the ablation index corresponds to an estimated depth of the lesion.

Clause 56: The system of any of Clauses 49-55, wherein the ablation index corresponds to an estimated diameter of the lesion.

Clause 57: The system of any of Clauses 49-56, the system further comprising: an alternating current (AC) signal generator configured to provide radiofrequency signals at high power; and a direct current (DC) signal generator configured to provide high voltage pulses.

Clause 58: The system of Clause 57, wherein the radiofrequency signals and the high voltage pulses are applied either sequentially or simultaneously to the organ tissue.

Clause 59: The system of Clause 57 or 58, wherein the radiofrequency signals are applied with a contact force of approximately 5 grams or more.

Clause 60: The system of any of Clauses 57-59, wherein the radiofrequency signals are provided of at least 25 Watts of power.

Clause 61: The system of any of Clauses 57-60, wherein the radiofrequency signals include a frequency from 350 kHZ to about 500 kHZ and the radiofrequency signals are provided for a duration of at least 1 second.

Clause 62: The system of any of Clauses 57-61, wherein the high voltage pulses include an amplitude of at least 800 V.

Clause 63: The system of any of Clauses 57-62, wherein a duration of each of the high voltage pulse is less than 20 microseconds.

Clause 64: The system of any of Clauses 57-63, wherein a plurality of high voltage pulses provides a pulse train of approximately 100 microseconds.

Clause 65: The system of any of Clauses 57-64, wherein a time gap of any value selected from 0.3 to 1000 milliseconds is provided between adjacent pulse trains.

Clause 66: The system of any of Clauses 57-65, wherein a plurality of pulse trains provides a PFA burst.

Clause 67: The system of any of Clauses 57-65, wherein the PFA burst comprises any value from 2 to 100 pulse trains with a duration of the PFA burst comprising any value selected from zero to 500 milliseconds.

Clause 68: The system of any of Clauses 57-66, wherein the high voltage pulse provides approximately 60 Joules or less.

Clause 69: The system of any of Clauses 49-68, wherein the predetermined effectiveness rate includes complication rates of 10% or less and is defined by existence or non-existence of asymptomatic cerebral embolic lesions at a discharge magnetic resonance imaging (MRI).

Clause 70: The system of any of Clauses 49-68, wherein the predetermined effectiveness rate includes complication rates of 8% or less and is defined by existence or non-existence of asymptomatic cerebral embolic lesions at a discharge magnetic resonance imaging (MRI).

Clause 71: The system of any of Clauses 49-68, wherein the predetermined effectiveness rate includes complication rates of 6% or less and is defined by existence or non-existence of asymptomatic cerebral embolic lesions at a discharge magnetic resonance imaging (MRI).

Clause 72: The system of any of Clauses 49-68, wherein the predetermined effectiveness rate includes complication rates of 5% or less and is defined by existence or non-existence of asymptomatic cerebral embolic lesions at a discharge magnetic resonance imaging (MRI).

Clause 73: The system of any of Clauses 49-68, wherein the predetermined effectiveness rate includes complication rates range from about 10% to about 1% and is defined by existence or non-existence of asymptomatic cerebral embolic lesions at a discharge magnetic resonance imaging (MRI).

Clause 74: The system of any of Clauses 49-73, wherein the predetermined effectiveness rate includes complication rates of approximately 0% and is defined by existence or non-existence of esophageal injury erythema.

Clause 75: The system of any of Clauses 49-74, wherein the predetermined effectiveness rate is approximately 100% and is defined by electrically isolating all targeted pulmonary veins without use of a focal ablation catheter.

Clause 76: The system of any of Clauses 49-74, wherein the predetermined effectiveness rate is approximately 98% and is defined by electrically isolating all targeted pulmonary veins without use of a focal ablation catheter.

Clause 77: The system of any of Clauses 49-74, wherein the predetermined effectiveness rate is approximately 96% and is defined by electrically isolating all targeted pulmonary veins without use of a focal ablation catheter.

Clause 78: The system of any of Clauses 49-74, wherein the predetermined effectiveness rate is approximately 94% and is defined by electrically isolating all targeted pulmonary veins without use of a focal ablation catheter.

Clause 79: The system of any of Clauses 49-74, wherein the predetermined effectiveness rate is approximately 92% and is defined by electrically isolating all targeted pulmonary veins without use of a focal ablation catheter.

Clause 80: The system of any of Clauses 49-79, wherein the predetermined effectiveness rate is defined by pulmonary vein isolation touch-up by a focal catheter among all targeted pulmonary veins.

Clause 81: The system of any of Clauses 49-80, wherein the predetermined effectiveness rate is defined by using focal catheter ablation for non-PV triggers during the pulmonary vein isolation.

Clause 82: The system of any of Clauses 49-81, wherein the predetermined effectiveness rate comprises a long-term effectiveness rate.

Clause 83: The system of any of Clauses 49-82, wherein the predetermined effectiveness rate is defined by an average number of radio frequency (RF) applications per vein and RF time required to isolate all pulmonary veins.

Clause 84: The system of any of Clauses 49-83, wherein the predetermined effectiveness rate is defined by an average number of RF applications per vein and RF time required to isolate common pulmonary veins.

Clause 85: The system of any of Clauses 49-84, wherein the predetermined effectiveness rate is defined by an average number of RF applications per patient and RF time required to isolate common pulmonary veins.

Clause 86: The system of any of Clauses 49-85, wherein the predetermined effectiveness rate is defined by determining incidence of complication rates being 10% or less of post-ablation symptomatic and asymptomatic cerebral emboli as compared to pre-ablation.

Clause 87: The system of any of Clauses 49-85, wherein the predetermined effectiveness rate is defined by determining incidence of complication rates being 8% or less of post-ablation symptomatic and asymptomatic cerebral emboli as compared to pre-ablation.

Clause 88: The system of any of Clauses 49-85, wherein the predetermined effectiveness rate is defined by determining incidence of complication rates being 5% or less of post-ablation symptomatic and asymptomatic cerebral emboli as compared to pre-ablation.

Clause 89: The system of any of Clauses 49-85, wherein the predetermined effectiveness rate is defined by determining incidence of complication rates ranging from about 8% to about 1% of post-ablation symptomatic and asymptomatic cerebral emboli as compared to pre-ablation.

Clause 90: The system of any of Clauses 49-89, wherein the effectiveness evaluation period is approximately seven days.

Clause 91: The system of any of Clauses 49-89, wherein the effectiveness evaluation period is approximately three months.

Clause 92: The system of any of Clauses 49-89, wherein the effectiveness evaluation period is approximately twelve months.

Clause 93: The system of Clause 49, further comprising: achieving an effectiveness rate of pulmonary vein isolation in approximately 97% of subjects in the group of patients within seven days of successful pulmonary vein isolation.

Clause 94: The system of Clause 49, further comprising: achieving an effectiveness rate of pulmonary vein isolation in approximately 96% of subjects in the group of patients within seven days of successful pulmonary vein isolation.

Clause 95: The system of Clause 49, further comprising: achieving an effectiveness rate of pulmonary vein isolation in approximately 95% of subjects in the group of patients within seven days of successful pulmonary vein isolation.

Clause 96: The system of Clause 49, further comprising: achieving an effectiveness rate of pulmonary vein isolation in approximately 94% of subjects in the group of patients within seven days of successful pulmonary vein isolation.

Clause 97: The system of Clause 49, further comprising: achieving an effectiveness rate of pulmonary vein isolation in approximately 65% of subjects in the group of patients within twelve months after atrial fibrillation.

Clause 98: The system of Clause 49, further comprising: achieving pulmonary vein isolation and at least a 97% safety endpoint within seven days of successful pulmonary vein isolation.

Clause 99: The system of Clause 49, further comprising: achieving pulmonary vein isolation and at least a 96% safety endpoint within seven days of successful pulmonary vein isolation.

Clause 100: The system of Clause 49, further comprising: achieving pulmonary vein isolation and at least a 95% safety endpoint within seven days of successful pulmonary vein isolation.

Clause 101: The system of Clause 49, further comprising: achieving pulmonary vein isolation and at least a 94% safety endpoint within seven days of successful pulmonary vein isolation.

Clause 102: The system of any of Clauses 49-101, wherein the processor is further configured to simulate an electric field produced by the pulsed field ablation to estimate a planned depth of the lesion.

Clause 103: A focal ablation catheter comprising: a tubular member extending along a longitudinal axis between a handle, a contact force sensor, and a tip electrode at a distal end of the tubular member, the tip electrode electrically connected to an energy generator configured to emit either a pulsed electric field or a radiofrequency signal to cardiac tissue through the tip electrode at one or more locations of cardiac tissue under control of a processor to ablate cardiac tissue, the contact force sensor being physically connected to the tip electrode and electrically connected to the processor to provide indication of a contact force experienced by the tip electrode against cardiac tissue during pulsed electric field ablation so that an ablation index is determined as a function of the measured contact force of the tip electrode and number of pulsed electric field applications for each location of the one or more locations in a heart.

Clause 104: The focal ablation catheter of Clause 103, wherein the pulsed field ablation index is determined by the formula:

$$AI_{PFA} = \sum_{i=0}^{n} [AI_n - AI_{n-1}],$$

where n is the number of applications of pulsed electric field applications and $AI_n$ is an index for each application of pulses and is defined by the formula: $AI_n = A*(B_n*\ln(\text{force}_n)+C_n)$, where A is a number ranging between 90 and 130, $B_n$ is a parameter determined by the formula: $B_n = B_0*\ln(n)+B_1$, and $C_n$ is a parameter determined by the formula: $C_n = C_0*\exp(C_1*n)$.

Clause 105: The catheter of Clause 104 wherein $B_0$ is equal to approximately 0.2653 and $B_1$ is equal to approximately 0.1623, and $C_0$ is equal to approximately 0.6862 and $C_1$ is equal to approximately 0.0867.

Clause 106: A system for applying pulsed field ablation to treat atrial fibrillation in a group of patients, the system comprising: a catheter comprising a tip electrode configured to emit a pulsed electric field or a radiofrequency signal to cardiac tissue and ablate one or more locations of cardiac tissue of the pulmonary vein; and a processor configured to: measure a contact force experienced by the tip electrode against cardiac tissue during pulsed electric field ablation, and determine a pulsed field ablation index as a function of the measured contact force and number of pulsed electric field applications for each location of the one or more locations.

Clause 107: The system of Clause 106, wherein the processor is further configured to calculate the pulsed field ablation index defined by the formula:

$$AI_{PFA} = \sum_{i=0}^{n} [AI_n - AI_{n-1}],$$

where n is the number of applications of pulsed electric field applications and $AI_n$ is an index for each application of pulses and is defined by the formula: $AI_n = A*(B_n*\ln(\text{force}_n)+C_n)$, where A is a number ranging between 90 and 130, $B_n$ is a parameter determined by the formula: $B_n = B_0*\ln(n)+B_1$, and $C_n$ is a parameter determined by the formula: $C_n = C_0*\exp(C_1*n)$.

Clause 108: The system of Clause 107, wherein $B_0$ is equal to approximately 0.2653 and $B_1$ is equal to approximately 0.1623, and $C_0$ is equal to approximately 0.6862 and $C_1$ is equal to approximately 0.0867.

Clause 109: The system of Clause 107, wherein the processor is further configured cease application of the pulsed field ablation applications in response to the calculated pulsed field ablation index reaching a prespecified target ablation index value.

Clause 110: The system of Clause 107, wherein the processor is further configured to present the pulsed field ablation index and the prespecified target ablation index value to a user.

Clause 111: The system of Clause 107, wherein the ablation index corresponds to an estimated volume of a lesion.

Clause 112: The system of Clause 107, wherein the ablation index corresponds to an estimated depth of the lesion.

Clause 113: The system of Clause 107, wherein the ablation index corresponds to an estimated diameter of the lesion.

Clause 114: The system of Clause 107, the system further comprising: an alternating current (AC) signal generator configured to provide radiofrequency signals at high power; and a direct current (DC) signal generator configured to provide high voltage pulses.

Clause 115: The system of Clause 107, wherein the radiofrequency signals and the high voltage pulses are applied either sequentially or simultaneously to the organ tissue.

Clause 116: The system of Clause 115, wherein the radiofrequency signals are applied with a contact force of approximately 5 grams or more.

Clause 117: The system of Clause 115, wherein the radiofrequency signals are provided of at least 25 Watts of power.

Clause 118: The system of Clause 115, wherein the radiofrequency signals include a frequency from 350kHZ to about 500 kHZ and the radiofrequency signals are provided for a duration of at least 1 second.

Clause 119: The system of Clause 115, wherein the high voltage pulses include an amplitude of at least 800 V.

Clause 120: The system of Clause 115, wherein a duration of each of the high voltage pulse is less than 20 microseconds.

Clause 121: The system of Clause 115, wherein a plurality of high voltage pulses provides a pulse train of approximately 100 microseconds.

Clause 122: The system of Clause 115, wherein a time gap of any value selected from 0.3 to 1000 milliseconds is provided between adjacent pulse trains.

Clause 123: The system of Clause 115, wherein a plurality of pulse trains provides a PFA burst.

Clause 124: The system of Clause 115, wherein the PFA burst comprises any value from 2 to 100 pulse trains with a duration of the PFA burst comprising any value selected from zero to 500 milliseconds.

Clause 125: The system of Clause 115, wherein the high voltage pulse provides approximately 60 Joules or less.

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A method of treating atrial fibrillation in a predetermined group of patients meeting predetermined inclusion and exclusion criteria, the method comprising:

delivering a catheter into a pulmonary vein of each patient of the predetermined group of patients, the catheter having a tip electrode configured to emit either a pulsed electric field or a radiofrequency signal to cardiac tissue and measure a contact force experienced by the tip electrode against cardiac tissue during pulsed electric field ablation;

ablating one or more locations of targeted tissues of the pulmonary vein using the catheter;

determining an ablation index as a function of the measured contact force and number of pulsed electric field applications for each location of the one or more locations from the pulsed electric field ablation; and achieving a predetermined effectiveness rate of pulmonary vein isolation in the predetermined group of patients within an effectiveness evaluation period.

2. The method of claim 1, wherein determining an ablation index for pulsed field ablation comprises calculating the ablation index $AI_{PFA}$ with:

$$AI_{PFA} = \sum_{i=0}^{n} [AI_n - AI_{n-1}],$$

where n is the number of applications of pulsed electric field applications and $AI_n$ is an index for each application of pulses and is defined by the formula:

$$AI_n = A * (B_n * \ln(\text{force}_n) + C_n),$$

where A is a number ranging between 90 and 130, $B_n$ is a parameter determined by the formula:

$$B_n = B_0 * \ln(n) + B_1, \text{ and}$$

$C_n$ is a parameter determined by the formula:

$$C_n = C_0 * \exp(C_1 * n).$$

3. The method of claim 2, wherein $B_0$ is equal to approximately 0.2653 and $B_1$ is equal to approximately 0.1623, and $C_0$ is equal to approximately 0.6862 and $C_1$ is equal to approximately 0.0867.

4. The method of claim 1, wherein the ablation index corresponds to an estimated volume of a lesion.

5. The method of claim 1, wherein the ablation index corresponds to an estimated depth of a lesion.

6. The method of claim 1, wherein the predetermined effectiveness rate is defined by a freedom from documented atrial fibrillation, atrial tachycardia, or atypical atrial flutter episodes based on electrocardiographic data through the effectiveness evaluation period.

7. The method of claim 1, wherein the predetermined effectiveness rate is defined by an average number of pulsed electric field (PF) applications per patient and contact force required to isolate all pulmonary veins.

8. The method of claim 1, wherein the predetermined effectiveness rate includes complication rates of 10% or less and is defined by existence or non-existence of asymptomatic cerebral embolic lesions at a discharge magnetic resonance imaging (MRI).

9. The method of claim 1, wherein the predetermined effectiveness rate is approximately 92% or greater defined by electrically isolating all targeted pulmonary veins without use of a focal ablation catheter.

10. The method of claim 1, wherein the predetermined effectiveness rate is defined by pulmonary vein isolation touch-up by a focal catheter among all targeted pulmonary veins.

11. The method of claim 1, wherein the predetermined effectiveness rate is defined by using focal catheter ablation for non-PV triggers during the pulmonary vein isolation.

12. The method of claim 1, wherein the predetermined effectiveness rate is defined by determining incidence of complication rates being 10% or less of post-ablation symptomatic and asymptomatic cerebral emboli as compared to pre-ablation.

13. The method of claim 1, further comprising:

achieving, by the catheter, an effectiveness rate of pulmonary vein isolation in approximately 94% or greater of subjects in the group of patients within seven days of successful pulmonary vein isolation.

14. The method of claim 1, wherein the delivering step comprises applying a contact force between the one or more targeted tissue and the catheter of about 5 grams to about 40 grams.

15. The method of claim 1, further comprising:

setting a power of the radio frequency signal to about 1 Watt to about 400 Watt;

maintaining the radio frequency signal for about 1 second to about 60 seconds; and generating, at the one or more locations of targeted tissues, a temperature change from about 20° C. to about 70° C.

16. A system for applying pulsed field ablation to treat atrial fibrillation in a group of patients, the system comprising:

a catheter comprising a tip electrode configured to emit a pulsed electric field or a radiofrequency signal to cardiac tissue and ablate one or more locations of cardiac tissue of a pulmonary vein; and a processor configured to:

measure a contact force experienced by the tip electrode against cardiac tissue during pulsed electric field ablation, and determine a pulsed field ablation index as a function of the measured contact force and number of pulsed electric field applications for each location of the one or more locations, wherein the system is configured to achieve a predetermined effectiveness rate of pulmonary vein isolation in the group of patients within an effectiveness evaluation period.

17. The system of claim 16, wherein the processor is further configured to cease application of the pulsed field ablation applications in response to the calculated pulsed field ablation index reaching a prespecified target ablation index value.

18. The system of claim 16, the system further comprising:

an alternating current (AC) signal generator configured to provide radiofrequency signals at high power; and a direct current (DC) signal generator configured to provide high voltage pulses.

19. The system of claim 18, wherein the radiofrequency signals and the high voltage pulses are applied either sequentially or simultaneously to the cardiac tissue.

20. The system of claim 19, wherein the radiofrequency signals are applied with a contact force of approximately 5 grams or more.

* * * * *